United States Patent
Perruche et al.

(10) Patent No.: US 11,793,865 B2
(45) Date of Patent: *Oct. 24, 2023

(54) CULTURED PHAGOCYTE SUPERNATENT COMPOSITIONS

(71) Applicants: INSTITUT NATIONAL DE LA SANTE ET DE LA RECHERCHE MEDICALE (INSERM), Paris (FR); ETABLISSEMENT FRANCAIS DU SANG, La Plaine Saint Denis (FR); UNIVERSITE DE FRANCHE-COMTE, Besancon (FR); CENTRE HOSPITALIER REGIONAL UNIVERSITAIRE DE BESANCON, Besancon (FR)

(72) Inventors: Sylvain Perruche, Placey (FR); Philippe Saas, Besancon (FR); Francis Bonnefoy, Besancon (FR)

(73) Assignees: INSTITUT NATIONAL DE LA SANTE ET DE LA RECHERCHE MEDICALE (INSERM), Paris (FR); ETABLISSEMENT FRANCAIS DU SANG, La Plaine Saint Denis (FR); UNIVERSITE DE FRANCHE-COMTE, Besançon (FR); CENTRE HOSPITALIER REGIONAL UNIVERSITAIRE BESANCON, Besançon (FR)

( * ) Notice: Subject to any disclaimer, the term of this patent is extended or adjusted under 35 U.S.C. 154(b) by 141 days.

This patent is subject to a terminal disclaimer.

(21) Appl. No.: 16/847,829

(22) Filed: Apr. 14, 2020

(65) Prior Publication Data
US 2020/0237884 A1    Jul. 30, 2020

Related U.S. Application Data

(63) Continuation of application No. 14/759,452, filed as application No. PCT/EP2014/050167 on Jan. 7, 2014, now Pat. No. 10,653,758.

(30) Foreign Application Priority Data

Jan. 7, 2013    (EP) .................................. 13305009

(51) Int. Cl.
| A61K 35/15 | (2015.01) |
| A61K 39/00 | (2006.01) |
| C07K 2/00 | (2006.01) |
| C07K 4/12 | (2006.01) |
| C07K 14/435 | (2006.01) |
| A61K 38/00 | (2006.01) |

(52) U.S. Cl.
CPC .......... *A61K 39/0005* (2013.01); *A61K 35/15* (2013.01); *A61K 38/00* (2013.01); *C07K 2/00* (2013.01); *C07K 4/12* (2013.01); *C07K 14/435* (2013.01)

(58) Field of Classification Search
None
See application file for complete search history.

(56) References Cited

FOREIGN PATENT DOCUMENTS

| WO | 2006/117786 A1 | 11/2006 |
| WO | 2006/120439 A2 | 11/2006 |
| WO | 2008/043018 A1 | 4/2008 |
| WO | 2010/070105 A1 | 6/2010 |

OTHER PUBLICATIONS

Bonnefoy et al., "Plasmacytoid dendritic cells play a major role in apoptotic leukocyte-induced immune modulation," Journal of Immunology, May 15, 2011, vol. 186, No. 10, pp. 5696-5705.
Perruche et al., "Apoptotic cell-mediated suppression of streptococcal cell wall-induced arthritis is associated with alteration of macrophage function and local regulatory T-cell increase: a potential cell-based therapy?" Arthritis Research and Therapy, Jul. 2, 2009, vol. 11, No. 4, 8 pages.
Michlewska et al., "Macrophage phagocytosis of apoptotic neutrophilis is critically regulated by the opposing action of pro-inflammatory and anti-inflammatory agents: key role for TNF-alpha," FASEB Journal: Official Publication of the ederation of American Societies for Experimental Biology, Mar. 2009, vol. 23, No. 3, pp. 844-854.
Perruche et al., "L14. Immunomodulatory properties of apoptotic cells," Presse Medicale, Apr. 2013, vol. 42, No. 4, pp. 537-543.

*Primary Examiner* — G. R. Ewoldt
(74) *Attorney, Agent, or Firm* — Oliff PLC

(57) ABSTRACT

A composition including a supernatant obtained from coculture of phagocytes with apoptotic cells. The composition is obtained by a) providing phagocytes, b) providing apoptotic cells, c) optionally washing the cells from step a) and b), d) co-culturing the cells of step a) and b), and e) separating the supernatant from the cells. The composition may be used in preventing or treating a pathological immune response.

11 Claims, 12 Drawing Sheets

Figure 1:
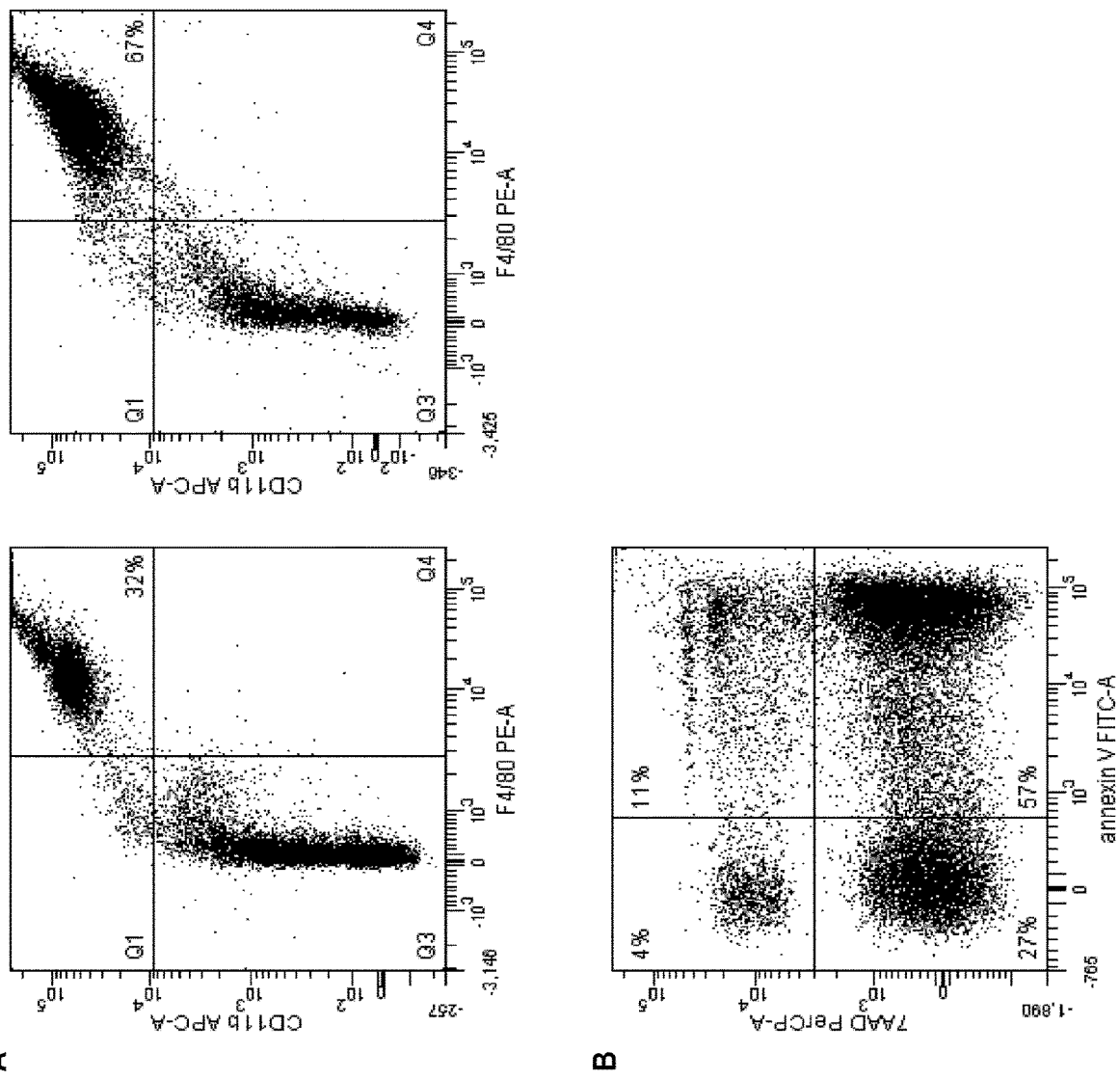

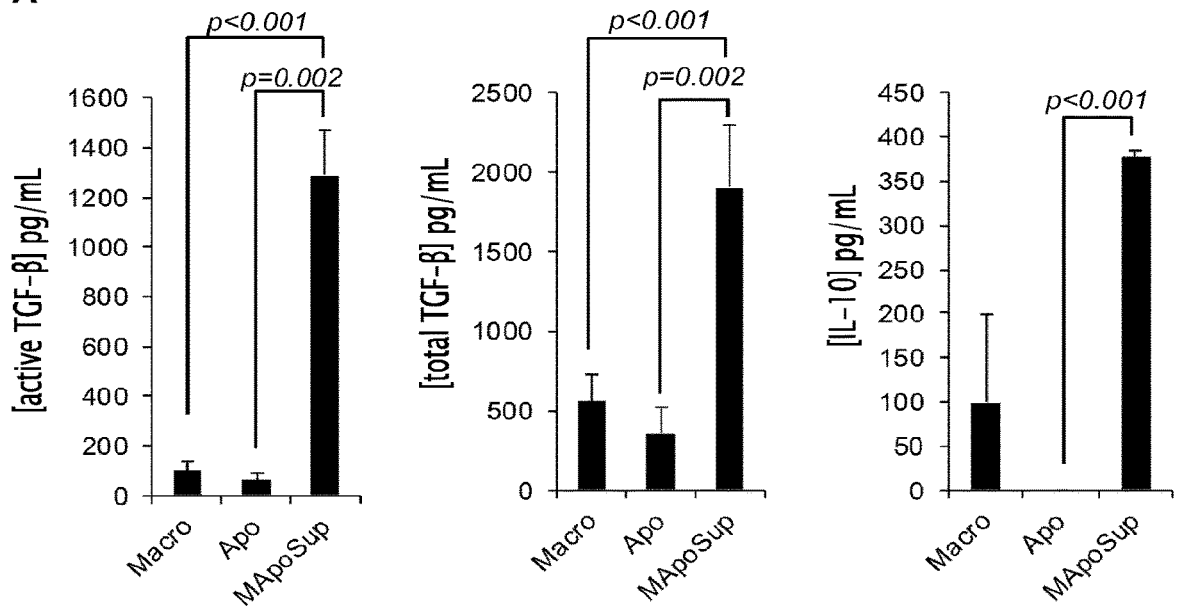
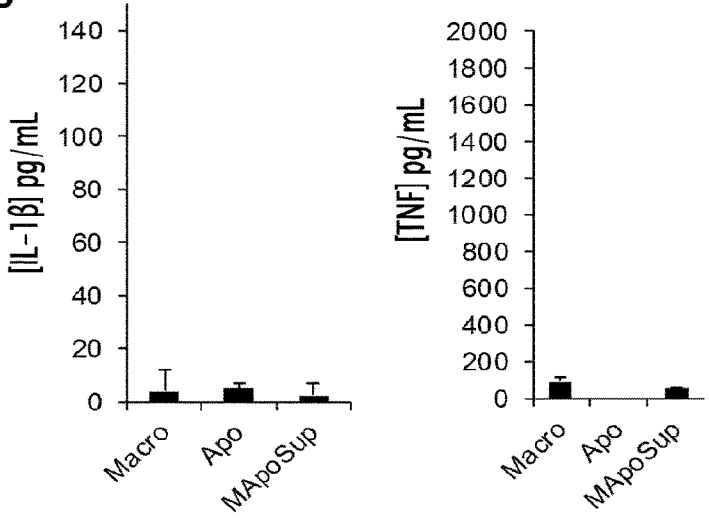
FIG.2

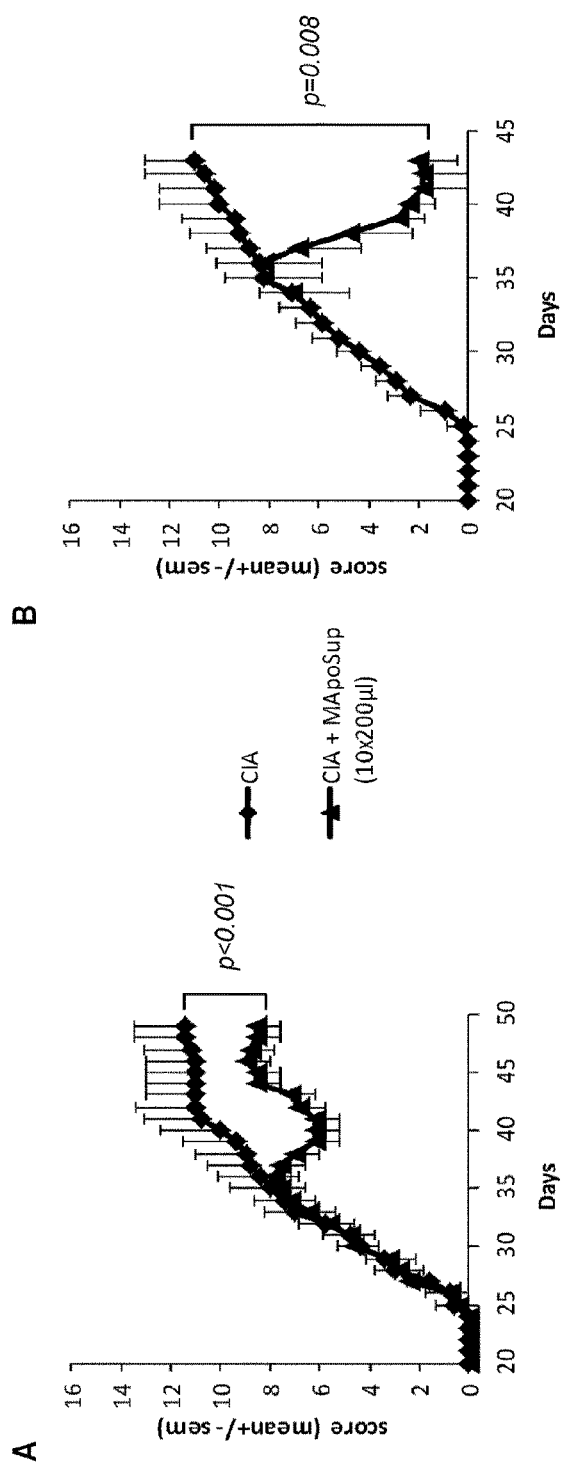
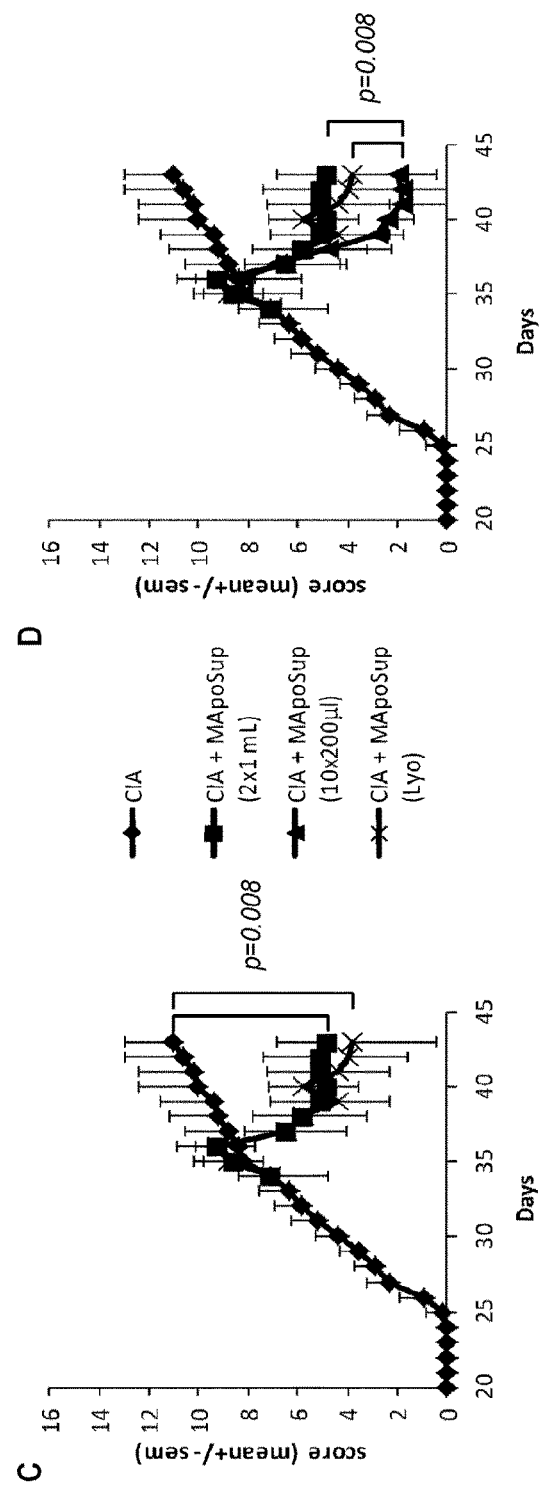
FIG.3

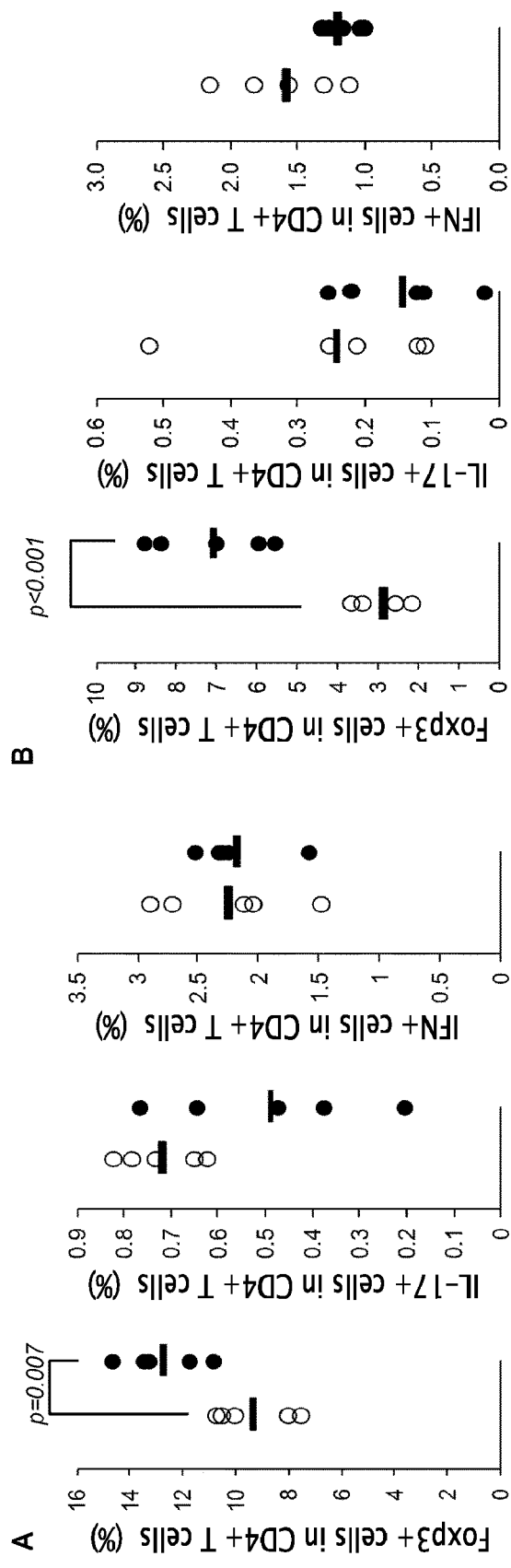
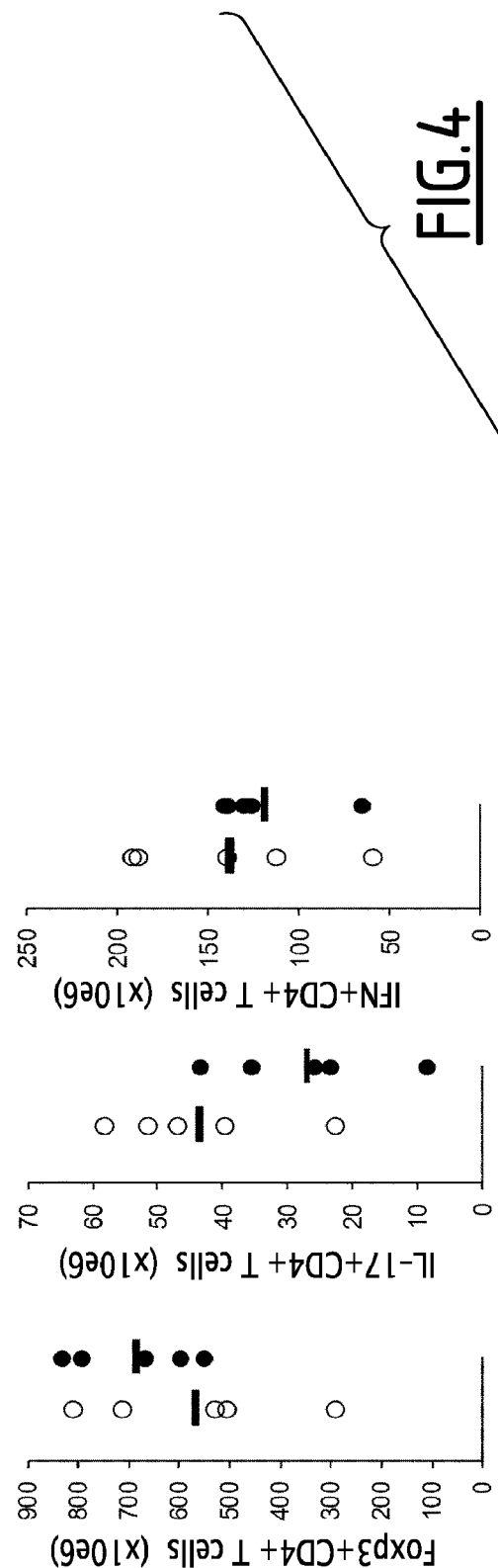
FIG. 4

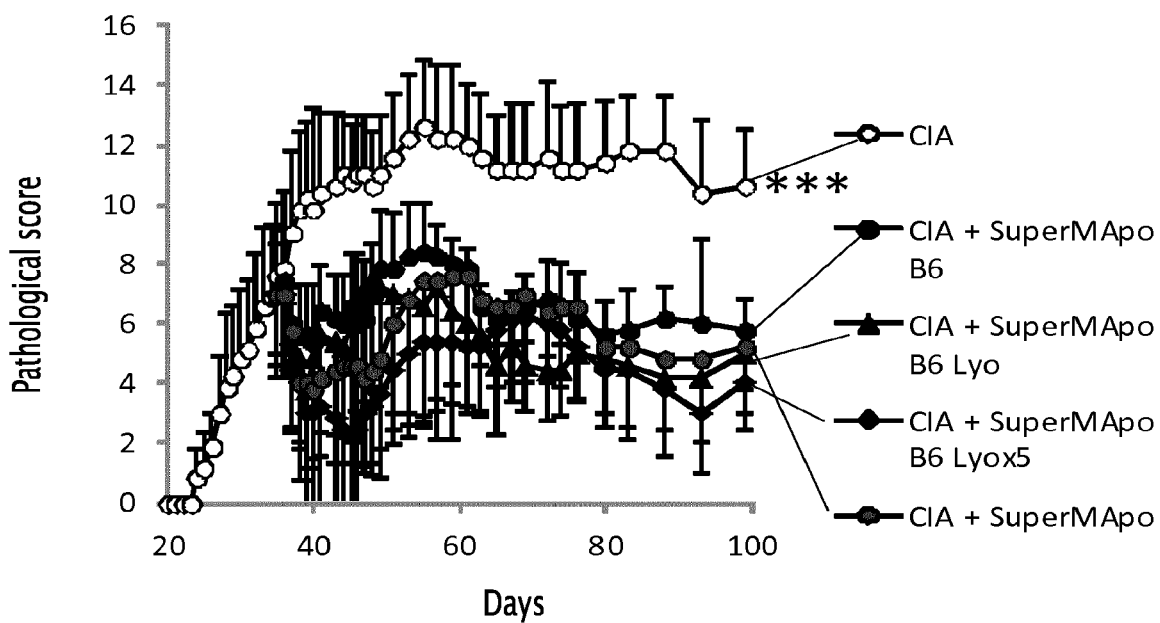
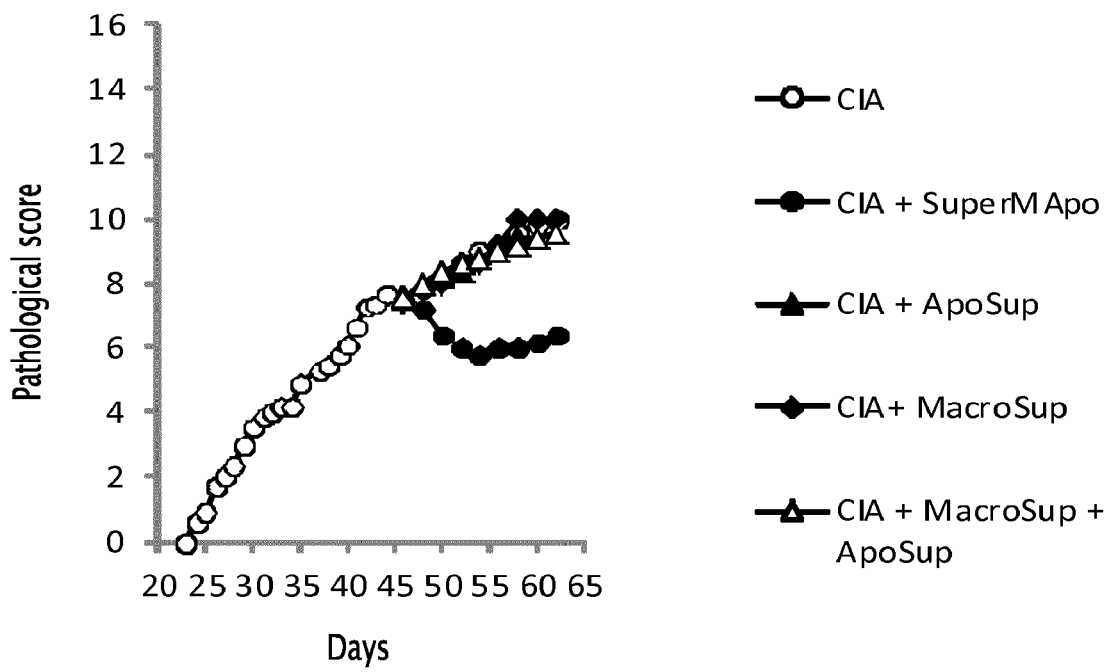
FIG.9

CULTURED PHAGOCYTE SUPERNATENT COMPOSITIONS

This is a Continuation of U.S. application Ser. No. 14/759,452 filed Jul. 7, 2015, which in turn is a National Stage Application of PCT/EP2014/050167 filed Jan. 7, 2014, which claims the benefit of European Application No. 13305009.6 (filed Jan. 7, 2013). The disclosures of the prior applications are hereby incorporated by reference herein in their entireties.

FIELD OF THE INVENTION

The present invention concerns pharmaceutical preparations to treat diseases characterized by a pathological immune response, methods of treatments using such preparations and processes for preparing said pharmaceutical preparations.

BACKGROUND TO THE INVENTION

The present invention relates to pharmaceutical preparations useful in the treatment of diseases characterized by a pathological immune response, and processes preparing such pharmaceutical preparations.

Diseases characterized by pathological immune responses include a large number of diseases which are associated with significant mortality and morbidity, and for which no satisfactory treatments are available. Such diseases particularly include autoimmune diseases, such as rheumatoid arthritis (RA) or inflammatory bowel disease (IBD), transplantation-related diseases such as graft-versus-host disease (GVHD).

These diseases result from a conflict of the immune system in which tolerogenic mechanisms controlling homeostasis have been disrupted. Many factors can be a source of such diseases, notably environmental factors, genetic predispositions as well as unresolved inflammation. Indeed, immune cells have the ability to sense bacteria, viruses and other foreign antigens and mount a strong immune response on the one hand, and on the other hand are able to sense self-derived antigens and tolerate them.

In addition to fighting infections, the immune system has the role of maintaining the normal state of health and function of the body. Therefore, throughout the life span of an organism, tissues become reshaped with areas of cells being removed. This is accomplished by a process termed programmed cell-death or apoptosis, the apoptotic cells disintegrate in an orderly and harmless fashion and are phagocytosed. This process of apoptosis is considered to be particularly important in the development and maintenance of the immune system itself, where immune cells which recognize or attack normal cells of the body are destroyed and removed by this process.

Cells which eliminate such unwanted cells are called professional phagocytes. Said professional phagocytes are recruited by several mechanisms and eliminate unwanted cells in order to maintain homeostasis and prevent inflammation.

Cells undergoing death by apoptosis have been shown to demonstrate immunomodulatory properties. Apoptosis is a physiological mechanism that eliminates cells in excess or cells that become undesirable without inducing an inflammatory response. The lack of inflammation associated with apoptosis is attributed to the fact that professional phagocytes, such as macrophages and immature dendritic cells efficiently eliminate apoptotic cells or blebs, thus preventing the release of proteases and other inflammatory mediators such as alarmines, and secondary necrosis of apoptotic cells, another proinflammatory event. This process of efficient apoptotic cell elimination is associated with mechanisms to prevent the initiation of immune responses. These mechanisms are critical and act in parallel since they should prevent the occurrence of autoimmune diseases. Two types of mechanisms can be distinguished: those related to apoptotic cells and those that are related to their elimination by phagocytes.

It has been reported that apoptotic cells, during the process of apoptosis, secrete immunosuppressive cytokines such as IL-10 and TGF-β. TGF-β, stored in a latent form in intracellular compartments, is released during the apoptotic process. These cytokines help to generate an immunosuppressive microenvironment, inhibit the secretion of proinflammatory cytokines (TNF-α or IL-1β) by macrophages and neutralize the induction of an effective immune response. This prevents the initiation of an immune response to self-antigens and prevents autoimmune response development. Apoptotic cells bind inflammatory chemokines such as CCL3 and CCL5 through the expression of CCR5, thus preventing the attraction of other leukocytes. These mechanisms are transient until apoptotic cells are eliminated/engulfed.

Recent publications showed that apoptotic cells also indirectly allow the induction of an immunomodulatory microenvironment through professional phagocytes. Indeed, phagocytes such as macrophages can release, or express immunosuppressive molecules (IL-10, TGF-β, prostaglandin E2, or PGE-2, Fas ligand) during the clearance of apoptotic cells (Griffith, T S and Ferguson, T A, *Immunity* (2011) 35: 456).

These phagocytes exert immunomodulatory effects to prevent the development of deleterious immune responses to the host. In addition, phagocytes eliminating apoptotic cells also spread this immunomodulatory message to adaptive immunity cells. Macrophages seem to be the main effective phagocytes that remove apoptotic cells.

Indeed, they express a large number of membrane receptors involved in this elimination. Stimulation of these receptors participates in the immunomodulatory properties associated with the removal of apoptotic cells. Numerous immunomodulatory mechanisms have been reported. They are characterized mainly by the release of soluble factors, cytokines such as IL-10 or TGF-β. The response of macrophages to danger stimuli is inhibited once they have removed the apoptotic cells. Certain subpopulations of dendritic cells are also involved in the capture of apoptotic cells. One study conducted on rats, showed that a subpopulation of circulating dendritic cells are responsible for continuously capturing apoptotic cells and bodies from intestinal epithelial cells removed each day after desquamation. Then, the dendritic cells migrate to the mesenteric lymph nodes where they inactivate autoreactive naïve T cells. Other studies, in the mouse model, also suggest that the capture of apoptotic cells by dendritic cells leads to tolerance. Moreover, an in vitro study showed that dendritic cells that have captured apoptotic cells did not respond to lipopolysaccharide (Morelli, A E and Larregina, A T, *Apoptosis* (2010) 15: 1083).

The consequences of apoptotic cell/phagocyte interaction influence the polarization of CD4+ T cells. Although contact with apoptotic cells inhibits the maturation and cytokine production of conventional dendritic cells, their migration capabilities are not affected. Thus, these cells can acquire CCR7 expression and migrate in response to gradients of CCL19 and CCL21 to the lymph nodes closest to the site where the cells die. In lymph nodes, dendritic cells having seen apoptotic cells can interact with naive CD4+ T cells and therefore favor their conversion to a regulatory phenotype such as regulatory T cells (Treg) through an immunomodulatory "message". A major characteristic of Treg generated by "immunomodulatory" dendritic cells is their ability to increased IL-10. It was also suggested that plasmacytoid dendritic cells are antigen presenting cells at the origin of Tr1 cells. However, these dendritic cells can also promote the differentiation of FoxP3+ Treg, notably in an apoptotic cell-rich microenvironment.

Traditional methods to treat diseases characterized by a pathological immune response with immunosuppressive drugs such as corticosteroid, azathiopine, cyclophosphamide, methotrexate and cyclosporine are far from being ideal treatments. The drug therapy is accompanied by serious side effects, including general immune suppression, leading to high rates of morbidity and being the primary cause of premature mortality. Furthermore, currently used immunosuppressive drugs have shown little or no impact on chronic rejection such as allograft rejection and graft-versus-host disease and therefore on overall long-term allograft survival. Importantly, long-term pharmacological immunosuppression is associated with toxicity and increased incidence of malignancies and infectious and metabolic diseases.

Therefore, the discovery of alternative ways for the manipulation of the immune system to treat such immune diseases has been a major goal for many years.

Apoptotic cells favour an immunosuppressive microenvironment through several mechanisms as described above. Therefore, several strategies using apoptotic cells for manipulating the immune system have already been proposed. The patent application WO2006/117786, for example, discloses injections of a cell preparation comprising dying or dead leukocytes to treat diseases associated with pathological immune responses.

However, the injection of cells suffers from various drawbacks such as the requirement for administration of allogeneic apoptotic cells, which is associated with the risk of allo-immunization favoring graft rejection since apoptotic cells have been demonstrated as an source of allo-antigens, and the failure to demonstrate adequate safety with respect to potential for inflammatory side-effects.

The patent application WO2010/070105 discloses an approach supposed to circumvent the problem of injecting cells into a subject. The application suggests using the supernatant of apoptotic cells to manipulate a subject's immune system. Nevertheless, recent research showed that the supernatant of apoptotic cells alone fails to activate for example plasmacytoid dendritic cells which are important to favor tolerance induction by mechanisms including regulatory T-Cell (Treg) induction (Bonnefoy F et al. J Immunol. 2011; 186(10):5696-705).

The patent WO2007/0559922 addresses this aspect and uses supernatant of apoptotic cells ex-vivo in order to generate regulatory T-cells which are then administered to the subject in need, especially subjects suffering from graft-versus-host diseases. Nevertheless, this application also suffers from drawbacks associated with the injection of foreign cell material into a subject, such as potential for inflammatory side-effects.

Thus, all the previous approaches have failed to provide standardized and efficient treatment of such diseases. Indeed, the therapeutic effect of apoptotic cell injection is strongly associated with apoptotic cell removal, therefore depending on the migration of apoptotic cells to phagocytic tissues, efficiency of phagocytes to remove apoptotic cells and of importance, the ability of phagocytes to generate such a tolerogenic environment.

Thus, it would be highly advantageous to propose a pharmaceutical preparation independent of such limitations.

DESCRIPTION OF THE INVENTION

The inventors have shown in vivo that a supernatant obtained from co-culture of phagocytes with apoptotic cells is surprisingly efficient in the treatment in mouse models of systemic autoimmune diseases and/or antibody-mediated autoimmune diseases such as rheumatoid arthritis as well as transplantation-related diseases such as graft-versus-host disease (GVHD). The use of such a supernatant provides a possible alternative to apoptotic cell injection in therapy of immune conditions which is potentially safer and more convenient.

Thus, the invention relates to a pharmaceutical preparation for use in preventing or treating a pathological immune response, comprising a supernatant obtainable from co-culture of phagocytes with apoptotic cells.

Said supernatant may be obtainable by a method comprising the following steps of a) providing phagocytes, b) providing apoptotic cells, c) optionally washing the cells from step a) and b), d) co-culturing the cells of step a) and b), and optionally e) separating the supernatant from the cells.

By "apoptotic cells" are meant any cells chosen from any cell type of a subject or any commercially available cell line subjected to a method of apoptosis induction known to the person skilled in the art. Said method of apoptosis induction is such as hypoxia, ozone, heat, radiation, chemicals, osmotic pressure, pH shift, X-ray irradiation, gamma-ray irradiation, UV irradiation, serum deprivation, corticoids or combinations thereof, wherein the method is not limited to said examples.

In an embodiment said apoptotic cells are leukocytes.

In an embodiment, said leukocytes and/or phagocytes derive from peripheral blood mononuclear cells (PBMC).

In an embodiment, said apoptotic cells and phagocytes are cultured individually prior to the co-culture step.

In an embodiment, co-culture of apoptotic cells and phagocytes takes place in a physiological solution.

During said co-culture step d) phagocytes and apoptotic cells are co-cultured, in one example they are co-cultured in a ratio of 1:5 (phagocytes to apoptotic cells), wherein the co-culture step d) is not limited to said ratio.

The supernatant may be "inactivated" prior to use, for example by irradiation. Therefore, the method for preparing the pharmaceutical preparation may comprise an optional additional irradiation step f).

In an embodiment, said pharmaceutical preparation is adapted for intra-cardiac administration, intra-arterial administration, subcutaneous administration, intramuscular administration, intra-organ administration or intravenous administration.

Also provided is a pharmaceutical preparation for use in preventing or treating a pathological immune response, comprising said supernatant and a pharmaceutically acceptable excipient.

In one example said preparation is lyophilized, for example for storage at −80° C.

Said pathological immune response may be, without limitation, an inflammatory immune response, an autoimmune disease or a transplantation-related disease.

In one example said autoimmune disease is rheumatoid arthritis [RA] or inflammatory bowel disease [IBD] and said transplantation-related disease is graft-versus-host disease [GVHD].

Also provided is a method for treating or preventing a pathological immune response comprising administering to an individual in need thereof a therapeutically effective amount of said supernatant obtainable from co-culture of phagocytes with apoptotic cells as disclosed herein.

Also provided is the use of a supernatant obtainable from co-culture of phagocytes with apoptotic cells as declared herein for the manufacture of a medicament for the treatment or prevention of a pathological immune response.

The pharmaceutical preparation of the invention is preferably a tolerogenic pharmaceutical preparation, wherein "tolerocenic" means that the pharmaceutical preparation is capable of inducing immunological tolerance.

"Apoptosis" is a cell death process distinct from necrosis and is the programmed and orderly physiological elimination of cells, occurring, for example, during normal cell and tissue development, T-lymphocyte killing of pathogen-infected cells, and self-elimination of mutationally damaged cells. Apoptotic cells are characterized by distinct morphologic alterations in the cytoplasm and nucleus, chromatin cleavage at regularly spaced sites, and endonucleolytic cleavage of genomic DNA at internucleosomal sites. Apoptosis, according to the invention has to be distinguished from "necrosis", which is on the other hand an inherently pathological and pro-inflammatory process of cell death caused, typically but not exclusively, by the uncontrolled, progressive degradative action of enzymes following lethal cellular injury. Necrotic cells are typically characterized by mitochondrial swelling, nuclear flocculation, cell lysis, loss of membrane integrity, and ultimately cell death. Necrosis can be identified, by light, fluorescence or electron microscopy techniques, or via uptake of the dye trypan blue.

The aforementioned properties of apoptotic cells stand in sharp contrast to those of necrotic cells, since necrosis is inherently a pathological process that is associated with generation of pro-inflammatory "danger" signals serving to stimulate—as opposed to suppress—immune responses for the body's defense.

Apoptosis of a cell can be confirmed by any of various commonly employed methods. Such methods include gel electrophoresis of cellular DNA to detect apoptosis-specific ladder-like DNA fragment patterns, TUNEL-staining to detect apoptosis-specific DNA fragmentation, staining with an annexin-fluorophore conjugate to detect apoptosis-specific reversal of cell membrane orientation, such as annexin V staining, staining with anti-cleaved caspase-3 antibody for detection of apoptosis-specific caspase activation, microscopic inspection to detect apoptosis-specific cellular fragmentation and blebbing, 7-ADD exclusion and the like. Preferably, apoptotic cells can be distinguished from other cells by annexin V staining and 7-AAD exclusion. Apoptotic cells are not permissive to trypan blue dye staining.

Cells undergoing apoptosis are referred to herein as apoptotic cells.

"Apoptotic cells" may be provided by methods known to the artisan for producing apoptotic cells by apoptosis induction. Said methods of apoptosis induction include hypoxia, ozone, heat, radiation, chemicals, osmotic pressure, pH shift, X-ray irradiation, gamma-ray irradiation, UV irradiation, serum deprivation, corticoids or combinations thereof.

Any cells may be used to obtain apoptotic cells. Therefore cells for the production of apoptotic cells can be selected from the following group of cells, without limiting to, exocrine secretory epithelial cells, hormone secreting cells, keratinizing epithelial cells, sensory transducer cells, autonomic neuron cells, sense organ and peripheral neuron supporting cells, central nervous system neurons and glial cells, lens cells, metabolism and storage cells, barrier function cells, extracellular matrix cells, contractile cells, blood and immune system cells, germ cells, nurse cells, interstitial cells. Furthermore, such cells can be derived from any commercially available cell lines.

Apoptosis induction, may be carried out over, for example several hours to several days, e.g. 2, 4, 6, 8, 10, 12, 14, 16, 18, 20, 22, 24, 26, 28, 30, 32, 34, 36, 38, 40, 42, 44, 46, 48, 50, 52 hours in an appropriate culture media.

A preparation of apoptotic cells may also comprise non-apoptotic cells, as apoptotic induction might be incomplete. Apoptotic cells will represent 20%-100% of the total cells, for example 20, 25, 30, 35, 40, 45, 50, 55, 60, 65, 70, 72, 74, 76, 78, 80, 82, 84, 86, 88, 90, 92, 94, 96, 98, 100%. Apoptotic cells will represent preferably 70%-100% of the total cells, for example 70, 72, 74, 76, 78, 80, 82, 84, 86, 88, 90, 92, 94, 96, 98, 100%.

It will be understood that the choice of culture medium for the apoptotic cells will be decided by the person skilled in the art depending on the type of cells which were subjected to an apoptosis induction. The culture medium is for example, without limitation to, RPMI, DMEM, X-vivo or Ultraculture milieus.

In one embodiment of the invention, the apoptotic cells are leukocytes.

According to one embodiment of the invention, the apoptotic cells are provided by selecting non-adherent leukocytes and submitting them to apoptosis induction, followed by a cell culture step in culture medium.

"Leukocytes" used to practice the method of the present invention may be derived from any lineage, or sub-lineage, of nucleated cells of the immune system and/or hematopoietic system, including but not limited to dendritic cells, macrophages, mast cells, basophils, hematopoietic stem cells, bone marrow cells, natural killer cells, and the like. Leukocytes of the present invention may be derived or obtained in any of various suitable ways, from any of various suitable anatomical compartments, according to any of various commonly practiced methods, depending on the application and purpose, desired leukocyte lineage, etc. Preferably, the source leukocytes are primary leukocytes, more preferably primary peripheral blood leukocytes.

Primary lymphocytes and monocytes may be most conveniently derived from peripheral blood. Peripheral blood leukocytes include 70-95 percent lymphocytes, and 5-25 percent monocytes.

Methods for obtaining specific types of source leukocytes from blood are routinely practiced. Obtaining source lymphocytes and/or monocytes can be achieved, for example, by harvesting blood in the presence of an anticoagulant, such as heparin or citrate. The harvested blood is then centrifuged over a Ficoll cushion to isolate lymphocytes and monocytes at the gradient interface, and neutrophils and erythrocytes in the pellet. Leukocytes may be separated from each other via standard immunomagnetic selection or immunofluorescent flow cytometry techniques according to their specific surface markers, or via centrifugal elutriation. For example, monocytes can be selected as the CD14+ fraction, T-lymphocytes can be selected as CD3+ fraction, B-lymphocytes can be selected as the CD19+ fraction, macrophages as the CD206+ fraction.

Lymphocytes and monocytes may be isolated from each other by subjecting these cells to substrate-adherent conditions, such as by static culture in a tissue culture-treated culturing recipient, which results in selective adherence of the monocytes, but not of the lymphocytes, to the cell-adherent substrate.

Leukocytes may also be obtained from peripheral blood mononuclear cells (PBMCs), which may be isolated as described herein.

One of ordinary skill in the art will possess the necessary expertise to suitably culture primary leukocytes so as to generate desired quantities of cultured source leukocytes of the present invention, and ample guidance for practicing such culturing methods is available in the literature of the art.

One of ordinary skill in the art will further possess the necessary expertise to establish, purchase, or otherwise obtain suitable established leukocyte cell lines from which to derive the apoptotic leukocytes. Suitable leukocyte cell lines may be obtained from commercial suppliers, such as the American Tissue Type Collection (ATCC).

It will be evident to the person skilled in the art that source leukocytes should not be obtained via a technique which will significantly interfere with their capacity to produce the apoptotic leukocytes.

In another embodiment, apoptotic cells are apoptotic lymphocytes. Apoptosis of lymphocytes, such as primary lymphocytes, may be induced by treating the primary lymphocytes with serum deprivation, a corticosteroid, or irradiation. Preferably, inducing apoptosis of primary lymphocytes via treatment with a corticosteroid is effected by treating the primary lymphocytes with dexamethasone, more preferably with dexamethasone at a concentration of about 1 micromolar. Preferably, inducing apoptosis of primary lymphocytes via irradiation is effected by treating the primary lymphocytes with gamma-irradiation, more preferably with a dosage of about 66 rad. Such treatment results in the generation of apoptotic lymphocytes suitable for the co-culture step with phagocytes.

In a further embodiment, apoptotic cells are apoptotic monocytes, such as primary monocytes. To generate apoptotic monocytes the monocytes are subjected to in vitro conditions of substrate/surface-adherence under conditions of serum deprivation. Such treatment results in the generation of non-pro-inflammatory apoptotic monocytes suitable for the co-culture step with phagocytes.

The term "phagocytes" denotes cells that protect the body by ingesting (phagocytosing) harmful foreign particles, bacteria, and dead or dying cells. Phagocytes include for example cells called neutrophils, monocytes, macrophages, dendritic cells, and mast cells, preferentially dendritic cells and monocytes/macrophages. The phagocytes according to the invention may be dendritic cells (CD4+ HLA-DR+ Lineage-BDCA1/BDCA3+), macrophages (CD14+ CD206+ HLA-DR+), or derived from monocytes (CD14+). Techniques to distinguish these different phagocytes are known to the person skilled in the art.

In an embodiment, monocytes are obtained by a plastic adherence step. Said monocytes can be distinguished from B and T cells with the marker CD14+, whereas unwanted B cells express CD19+ and T cells CD3+. After Macrophage Colony Stimulating Factor (M-CSF) induced maturation the obtained macrophages are preferably positive for the markers CD14+, CD206+, HLA-DR+.

Phagocytes may be provided by any method known in the art for obtaining phagocytes. In one embodiment, phagocytes such as macrophages or dendritic cells can be directly isolated from a subject or be derived from precursor cells by a maturation step.

In one embodiment, macrophages are directly isolated from the peritoneum cavity of a subject and cultured in complete RRPMI medium.

Macrophages can also be isolated from the spleen.

Phagocytes are also obtainable from peripheral blood monocytes. In said example, monocytes when cultured differentiate into monocyte-derived macrophages upon addition of, without limitation to, macrophage colony stimulating factor (M-CSF) to the cell culture media.

For example, phagocytes may be derived from peripheral blood mononuclear cells (PBMC). For example, PBMC may be isolated from cytapheresis bag from an individual through Ficoll gradient centrifugation, plated in a cell-adherence step for 90 min in complete RPMI culture medium (10% FBS, 1% Penicillin/Streptomycin). Non-adherent cells are removed by a plastic adherence step, and adherent cells cultured in complete RPMI milieu supplemented with recombinant human M-CSF. After the culture period, monocyte-derived macrophages are obtained.

Phagocytes can be selected by a cell-adherence step. Said "cell adherence step" means that phagocytes or cells which can mature into phagocytes are selected via culturing conditions allowing the adhesion of the cultured cells to a surface, a cell adherent surface (e.g. a tissue culture dish, a matrix, a sac or bag with the appropriate type of nylon or plastic).

"Cell adherent surfaces" are preferably hydrophilic and negatively charged, and may be obtained in any of various ways known in the art, preferably by modifying a polystyrene surface using, for example, corona discharge, or gas-plasma. These processes generate highly energetic oxygen ions which graft onto the surface polystyrene chains so that the surface becomes hydrophilic and negatively charged. Culture recipients designed for facilitating cell-adherence thereto are available from various commercial suppliers (e.g. Corning, Perkin-Elmer, Fisher Scientific, Evergreen Scientific, Nunc, etc.).

The cell maturation of phagocytes takes place during cell culture, for example due to addition of maturation factors to the media. In one embodiment said maturation factor is M-CSF, which may be used for example to obtain monocyte-derived macrophages.

The culture step used for maturation or selection of phagocytes might take several hours to several days. Preferably said pre-mature phagocytes are cultured for 2, 4, 6, 8, 10, 12, 14, 16, 18, 20, 22, 24, 26, 28, 30, 32, 34, 36, 38, 40, 42, 44, 46, 48, 50, 52, 54, 56, 58 hours in an appropriate culture medium.

The culture medium for phagocytes is known to the person skilled in the art and can be for example, without limitation, RPMI, DMEM, X-vivo and Ultraculture milieus.

After cell culture the cells may be enriched for the specific type of phagocytes targeted by the culture conditions known to the person skilled in the art. Said phagocytes may represent 20%-100% of the total cells, for example, 20, 25, 30, 35, 40, 45, 50, 55, 60, 65, 70, 72, 74, 76, 78, 80, 82, 84, 86, 88, 90, 92, 94, 96, 98 and 100%. Said phagocytes represent preferably 60%-100% of the total cells, more preferably 60, 65, 70, 72, 74, 76, 78, 80, 82, 84, 86, 88, 90, 92, 94, 96, 98, and 100%.

The preparation according to the invention may contain the immunosupressants IL-10, TGF-β, Prostaglandins (such as E2, PGE-2), IL-1ra, TIMP-1, CXCL1/KC, CCL2/JE, CX3CL1 and/or MCP1.

Preferably the preparation does not contain pro-inflammatory mediators, for example IL-1, IL-6, and/or TNF.

"Immunosuppressants" or "anti-inflammatory compounds" according to the invention are any substances that perform an immune suppression of the immune system.

"Co-culture" as used herein means a cell culture containing growths of the same cell type but differently treated prior to cell culture or of at least two distinct cell types, preferably of at least two distinct cell types.

In case of the same cell type "differently treated" refers herein to the induction of apoptosis in one fraction of the cells but not in the other.

Prior to this "co-culture" the cells are submitted to a washing step. Preferably, phagocytes and apoptotic cells are washed before the co-culture step. In one embodiment, the cells are washed with PBS.

During said co-culture phagocytes and apoptotic cells may be mixed in a ratio of 10:1, 9:1; 8:1, 7:1, 6:1, 5:1, 4:1, 3:1, 2:1, 1:1, more preferably in a ratio of (phagocytes:apoptotic cells) 1:2, 1:3, 1:4, 1:5, 1:6, 1:7, 1:8, 1:9, 1:10. In one example, the ratio of phagocytes to apoptotic cells is 1:5.

The co-culture of the cells might be for several hours to several days. Preferably said apoptotic cells are cultured for 2, 4, 6, 8, 10, 12, 14, 16, 18, 20, 22, 24, 26, 28, 30, 32, 34, 36, 38, 40, 42, 44, 46, 48, 50, 52 hours.

A person skilled in the art can evaluate the optimal time for co-culture by measuring the presence of anti-inflammatory compounds, the viable amount of phagocytes and the amount of apoptotic cells which have not been eliminated so far.

The elimination of apoptotic cells by phagocytes is observable with light microscopy due to the disappearance of apoptotic cells.

Co-culture preferably takes place in culture medium and/or in a physiological solution compatible with administration e.g. injection to a subject.

A "physiological solution" is preferably a solution which does not lead to the death of phagocytes within the culture time. Preferably the physiological solution does not lead to death over 2, 4, 6, 8, 10, 12, 14, 16, 18, 20, 22, 24, 26, 28, 30, 32, 34, 36, 38, 40, 42, 44, 46, 48, 50, 52 hours, preferably 48 hours, more preferably 30 hours.

Preferably, the phagocytes and apoptotic cells are incubated in the physiological solution for at least 30 min. This time of culture allows phagocytosis initiation and secretion of cytokines and other beneficial substances.

If the number of viable phagocytes during co-culture in the physiological solution decreases by 75%, 80%, 85% or by 90% within one hour or 30 minutes, the solution is not considered to be a physiological solution as defined herein.

Additionally, such a physiological solution preferably does not inhibit apoptotic leukocyte elimination by leukocyte-derived macrophages.

At the end of the co-culture step, the supernatant is optionally separated from the co-cultured cells. Techniques to separate the supernatant from the cells are known in the art. For example, the supernatant can be collected and/or filtered and/or centrifuged to eliminate cells and debris. For example, said supernatant may be centrifuged at 3000 rpm for 15 minutes at room temperature to separate it from the cells.

In one embodiment, the separated supernatant is frozen or lyophilized for conservation and subsequent use.

The supernatant separated from the cells may be irradiated.

Said "irradiation" step can be considered as a disinfection method that uses X-ray irradiation (25-45 Gy) at sufficiently rate to kill microorganisms, as routinely performed to inactivate blood products.

For conservation, the final product may be either conserved at +4° C., preferably for use in the next 48 hours or lyophilized to enable storage at −80° C.

The preparation of the invention may additionally comprise a pharmaceutically acceptable excipient.

Thus, another aspect of the invention relates to a pharmaceutical preparation comprising the supernatant of the invention and a pharmaceutically acceptable carrier.

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and gender of the patient, etc.

The pharmaceutical compositions of the invention can be formulated for a topical, oral, parenteral, intranasal, intra-organ, intra-cardiac, intra-arterial, intravenous, intramuscular, subcutaneous or intraocular administration and the like.

In another embodiment, the pharmaceutical preparation according to the invention comprises at least one other immunosuppressant.

To prepare a pharmaceutical preparation, an effective amount of a lyophilized preparation may be dissolved or dispersed in a pharmaceutically acceptable carrier or aqueous medium.

The "carrier" can also be a solvent or dispersion medium containing, for example, water, ethanol, polyol (for example, glycerol, propylene glycol, and liquid polyethylene glycol, and the like), suitable mixtures thereof, and vegetables oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by either solubilizing the lyophilized supernatant in the required amount in the appropriate solvent with various of the other ingredients enumerated above, as required, followed by filtered sterilization or by directly filter sterilizing the pharmaceutical preparation comprising the supernatant.

In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as it is therapeutically effective. The formulations are easily administered in a variety of dosage forms, such as the type of injectable solutions described above, but drug release capsules and the like can also be employed.

In addition to the pharmaceutical preparation comprising a supernatant formulated for parenteral administration other pharmaceutically acceptable forms include, e.g. tablets or other solids for oral administration, time release capsules, and any other form currently used.

Depending on the application and purpose, disease treatment may be advantageously effected according to the teachings of the present invention in conjunction with standard prior art therapies.

During and after disease treatment according to the method of the present invention, disease status will preferably be closely monitored so as to optimize and suitably modify the treatment. For example, levels of any of various proinflammatory cytokines, chemokines or other molecules may be monitored in the patient to facilitate monitoring of disease treatment. In the case of autoimmune diseases, tissue levels of relevant autoantibodies may be measured for monitoring disease treatment. For example, in the case a systemic autoimmune disease, such as systemic lupus erythematosus, such autoantibodies include those specific for double-stranded DNA, and those specific for phospholipids.

One of ordinary skill in the art, such as a physician, preferably a specialist in the disease to be treated, will possess the necessary expertise for applying the teachings of the present invention so as to effectively treat a disease of the present invention in a human subject.

A "pathological immune response" may be an inflammatory immune response and other diseases including autoimmune diseases, transplantation-related diseases, and inflammation-associated diseases.

Examples of diseases characterized by pathological immune responses which can be treated according to the present invention are described below.

As used herein, the term "disease" refers to any medical disease, disorder, condition, or syndrome, or to any undesired and/or abnormal physiological morphological, cosmetic and/or physical state and/or condition.

As used herein, the term "treat" when relating to a disease of the present invention refers to preventing onset of the disease, alleviating, attenuating, palliating or eliminating the symptoms of a disease, slowing, reversing or arresting the progression of the disease, or curing the disease.

According to the invention, the term "subject" or "subject in need thereof" is intended for a human or non-human mammal affected or likely to be affected with an inflammatory disorder. In particular, said subject may be a patient who has been determined to be susceptible to a therapeutic preparation according to the invention, in particular to the immunosuppressant components present in the pharmaceutical preparation according to the invention, for instance according to a method as described here below.

The terms "subject", "individual" or "host" may be, for example, a human or a non-human mammal. For example, the subject is a bat; a ferret; a rabbit; a feline (cat); a canine (dog); a primate (monkey), an equine (horse); a human, including man, woman and child.

Preferably, the preparations and methods of the present invention are used to treat the disease in a subject.

By a "therapeutically effective amount" of the pharmaceutical preparation is meant a sufficient amount of the pharmaceutical preparation to treat said pathological immune response, at a reasonable benefit/risk ratio applicable to any medical treatment. It will be understood, however, that the total daily usage of the pharmaceutical preparation and compositions of the present invention will be decided by the attending physician within the scope of sound medical judgment. The specific therapeutically effective dose level for any particular patient will depend upon a variety of factors including the disorder being treated and the severity of the disorder; activity of the pharmaceutical preparation employed; the age, body weight, general health, sex and diet of the patient; the time of administration, route of administration; the duration of the treatment; drugs used in combination or coincidental with the specific preparation employed; and like factors well known in the medical arts. For example, it is well known within the skill of the art to start doses of the preparation at levels lower than those required to achieve the desired therapeutic effect and to gradually increase the dosage until the desired effect is achieved.

According to an embodiment, treatment of a disease of the present invention is effected by administering to the subject a pharmaceutical preparation which comprises a total dose or aliquot of supernatant derived from the co-culture of about 14*10e9 of CD45+ cells obtained by cytapheresis equivalent to about 200 million of cells per kilogram of body weight (for a 70 kg subject). Preferably, such a total dose is administered as unit doses of supernatant derived from about 100 million cells per kilogram body weight, and/or is administered as unit doses at weekly intervals, more preferably both of which. Suitable total doses according to this embodiment include total doses of supernatant derived from about 10 million to about 4 billion cells per kilogram body weight, more preferably supernatant derived from about 40 million to about 1 billion cells per kilogram body weight, more preferably supernatant derived from about 80 million to about 500 million cells per kilogram body weight, and more preferably supernatant derived from about 160 million to about 250 million cells per kilogram body weight. Suitable unit doses according to this embodiment include unit doses of supernatant derived from about 4 million to about 400 million cells per kilogram body weight, more preferably supernatant derived from about 8 million to about 200 million cells per kilogram body weight, more preferably supernatant derived from about 16 million to about 100 million cells per kilogram body weight, and more preferably supernatant derived from about 32 million to about 50 million cells per kilogram body weight.

Therefore, the preparations and methods of the present invention can be used to treat in any of various types of subjects and any of various diseases associated with a pathological immune response. Such diseases particularly include autoimmune diseases, transplantation-related diseases, and inflammation-associated diseases.

The auto-immune disease may be, for example, inflammatory bowel disease (IBD), a systemic autoimmune disease and/or an antibody-mediated auto-immune disease such as rheumatoid arthritis (RA) or a transplantation-related disease such as graft-versus-host disease (GVHD), or other condition described below.

The disease characterized by a pathological immune response may be any of various inflammatory/inflammation-associated diseases.

Examples of antibody-mediated autoimmune diseases include but are not limited to rheumatoid diseases, rheumatoid autoimmune diseases, rheumatoid arthritis (Krenn V. et al., Histol Histopathol 2000; 15(3): 791), spondylitis, ankylosing spondylitis (Jan Voswinkel et al., Arthritis Res 2001; 3(3): 189), systemic diseases, systemic autoimmune diseases, systemic lupus erythematous (Erikson J et al., Immunol Res. 1998; 17(1-2):49), sclerosis, systemic sclerosis (Renaudineau Y. et al., Clin Diagn Lab Immunol. 1999; 6(2):156); Chan 0 T. et al., Immunol Rev 1999; 169:107), glandular diseases, glandular autoimmune diseases, pancreatic autoimmune diseases, diabetes, type I diabetes (Zimmet P. Diabetes Res Clin Pract 1996; 34 Suppl: S125), thyroid diseases, autoimmune thyroid diseases, Graves' disease (Orgiazzi J. Endoerinol Metab Clin North Am 2000; 29(2): 339), thyroiditis, spontaneous autoimmune thyroiditis (Braley-Mullen H. and Yu S, J Immunol 2000; 165(12): 7262), Hashimoto's thyroiditis (Toyoda N. et al., Nippon Rinsho 1999; 57(8): 1810), myxedema, idiopathic myxedema (Mitsuma T. Nippon Rinsho. 1999; 57(8): 1759); autoimmune reproductive diseases, ovarian diseases, ovarian autoimmunity (Garza K M. et al., J Reprod Immunol 1998; 37(2): 87), autoimmune anti-sperm infertility (Diekman A B. et al., Am J Reprod Immunol. 2000; 43(3): 134), repeated fetal loss (Tincani A. et al., Lupus 1998; 7 Suppl 2: S107-9), neurodegenerative diseases, neurological diseases, neurological autoimmune diseases, multiple sclerosis (Cross A H. et al., J Neuroimmunol 2001; 112(1-2): 1), Alzheimer's disease (Oron L. et al., J Neural Transm Suppl. 1997; 49: 77), myasthenia gravis (Infante A J. And Kraig E, Int Rev Immunol 1999; 18(1-2): 83), motor neuropathies (Kornberg A J. J Clin Neurosci. 2000; 7(3): 191), Guillain-Barre syndrome, neuropathies and autoimmune neuropathies (Kusunoki S. Am J Med Sei. 2000; 319(4): 234), myasthenic diseases, Lambert-Eaton myasthenic syndrome (Takamori M. Am J Med Sci. 2000; 319(4): 204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. J. Rev Neural (Paris) 2000; 156(1): 23); neuropathies, dysimmune neuropathies (Nobile-Orazio E. et al., Electroencephalogr Clin Neurophysiol Suppl 1999; 50: 419); neuromyotonia, acquired neuromyotonia, arthrogryposis multiplex congenita (Vincent A. et al., Ann N Y Aead Sci. 1998; 841: 482), cardiovascular diseases, cardiovascular autoimmune diseases, atherosclerosis (Matsuura E. et al., Lupus. 1998; 7 Supp12: S135), myocardial infarction (Vaarala O. Lupus. 1998; 7 Supp12: S132), thrombosis (Tineani A. et al., Lupus 1998; 7 Supp12: S107-9), granulomatosis, Wegener's granulomatosis, arteritis, Takayasu's arteritis and Kawasaky syndrome (Praprotnik S. et al., Wien Klin Wochenschr 2000; 112(15-16): 660); anti-factor VIII autoimmune disease (Lacroix-Desmazes S. et al., Semin Thromb Hemost. 2000; 26(2): 157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000; 151(3): 178); antiphospholipid syndrome (Flamholz R. et al., J Clin Apheresis 1999; 14(4): 171); heart failure, agonist-like beta-adrenoceptor antibodies in heart failure (Wallukat G. et al., Am J Cardiol. 1999; 83 (12A): 75H), thrombocytopenic purpura (Moccia F. Ann Ital Med Int. 1999; 14 (2): 114); hemolytic anemia, autoimmune hemolytic anemia (Efrernov D G. et al., Leuk Lymphoma 1998; 28 (3-4): 285), gastrointestinal diseases, autoimmune diseases of the gastrointestinal tract, intestinal diseases, chronic inflammatory intestinal disease (Garcia Herola A. et al., Gastroenterol Hepatol. 2000; 23(1): 16), celiac disease (Landau Y B. and Shoenfeld Y. Harefuah 2000; 138(2): 122), autoimmune diseases of the musculature, myositis, autoimmune myositis, Sjogren's syndrome (Feist E. et al., Int Arch Allergy Immunol 2000; 123(1): 92); smooth muscle autoimmune disease (Zauli D. et al., Biomed Pharmacother 1999; 53(5-6): 234), hepatic diseases, hepatic autoimmune diseases, autoimmune hepatitis (Manns M P. J Hepatol 2000; 33(2): 326) and primary biliary cirrhosis (Strassburg C P. et al., Eur J Gastroenterol Hepatol. 1999; 11(6): 595).

Examples of organ/tissue specific autoimmune diseases comprise cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases. Examples of autoimmune cardiovascular diseases comprise atherosclerosis (Matsuura E. et al., Lupus. 1998; 7 Suppl 2: S135), myocardial infarction (Vaarala O. Lupus. 1998; 7 Suppl 2: S132), thrombosis (Tincani A. et al., Lupus 1998; 7 Suppl 2: S107-9), Wegener's granulomatosis, Takayasu's arteritis, Kawasaki syndrome (Praprotnik S. et al., Wien Klin Wochenschr 2000; 112(15-16): 660), anti-factor VIII autoimmune disease (Lacroix-Desmazes S. et al., Semin Thromb Hemost. 2000; 26(2): 157), necrotizing small vessel vasculitis, microscopic polyrulgiitis, Churg and Strauss syndrome, pauci-immune focal necrotizing and crescentic glomerulonephritis (Noel L H. Ann Med Interne (Paris). 2000; 151 (3): 178), antiphospholipid syndrome (Flamholz R. et al., J Clin Apheresis 1999; 14(4): 171), antibody-induced heart failure (Wallukat G. et al., Am J Cardiol. 1999; 83 (12A): 75H), thrombocytopenic purpura (Moccia F. Ann Ital Med Int. 1999; 14 (2): 114; Semple J W. et al., Blood 1996; 87(10): 4245), autoimmune hemolytic anemia (Efrernov D G. et al., Leuk Lymphoma 1998 January; 28(3-4): 285; Sallah S. et al., Ann Hemato 1997; 74(3): 139), cardiac autoimmunity in Chagas' disease (Cunha-Neto E. et al., J Clin Invest 1996; 98(8): 1709) and anti-helper T lymphocyte autoimmunity (Caporossi A P. et al., Viral Immunol 1998; 11(1): 9).

Examples of autoimmune rheumatoid diseases comprise rheumatoid arthritis (Krenn V. et al., Histol Histopathol 2000; 15(3): 791; Tisch R, McDevitt H O. Proc Nat Acad Sci units S A 1994; 91(2): 437) and ankylosing spondylitis (Jan Voswinkel et al., Arthritis Res 2001; 3(3): 189).

Examples of autoimmune glandular diseases comprise pancreatic disease, type diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and type 1 autoimmune polyglandular syndrome. Diseases comprise autoimmune diseases of the pancreas, type 1 diabetes (Castano L. and Eisenbarth G S. Ann. Rev. Immunol. 8: 647; Zimmet P. Diabetes Res Clin Pract 1996; 34 Suppl: S125), autoimmune thyroid diseases, Graves' disease (Orgiazzi J. Endocrinol Metab Clin North Am 2000; 29(2): 339; Sakata S. et al., Mol Cell Endocrinol 1993; 92(1): 77), spontaneous autoimmune thyroiditis (Braley-Mullen H. and Yu S, J Immunol 2000; 165(12): 7262), Hashimoto's thyroiditis (Toyoda N. et al., Nippon Rinsho 1999; 57(8): 1810), idiopathic myxedema (Mitsuma T. Nippon Rinsho. 1999; 57(8): 1759), ovarian autoimmunity (Garza K M. et al., J Reprod Immunol 1998; 37 (2): 87), autoimmune anti-sperm infertility (Diekman A B. et al., Am J Reprod Immunol. 2000; 43(3): 134), autoimmune prostatitis (Alexander R B. et al., Urology 1997; 50(6): 893) and type 1 autoimmune polyglandular syndrome (Hara T. et al., Blood. 1991; 77(5): 1127).

Examples of auto-immune gastrointestinal diseases comprise chronic inflammatory intestinal diseases (Garcia Herola A. et al., Gastroenterol Hepatol. 2000; 23(1): 16), celiac disease (Landau Y B. and Shoenfeld y. Harefuah 2000; 138(2): 122), colitis, ileitis and Crohn's disease.

Examples of auto-immune cutaneous diseases comprise auto-immune bullous skin diseases, such as, but not limited to, pemphigus vulgaris, bullous pemphigoid and pemphigus foliaceus, discoid lupus erythematous.

Examples of autoimmune hepatic diseases comprise hepatitis, auto-immune chronic active hepatitis (Franco A. et al., Clin Immunol Immunopathol 1990; 54(3): 382), primary biliary cirrhosis (Jones D E. Clin Sci (Colch) 1996; 91(5): 551; Strassburg C P. et al., Eur J Gastroenterol Hepatol. 1999; 11(6): 595) and autoimmune hepatitis (Manns M P. J Hepatol 2000; 33(2): 326).

Examples of auto-immune neurological diseases comprise multiple sclerosis (Cross A H. et al., J Neuroimmunol 2001; 112 (1-2): 1), Alzheimer's disease (Oron L. et al., J Neural Transm Suppl. 1997; 49: 77), myasthenia gravis (Infante Al And Kraig E, Int Rev Immunol 1999; 18(1-2): 83; Oshima M. et al., Eur J Immunol 1990; 20(12): 2563), neuropathies, motor neuropathies (Kornberg A J. J Clin Neurosci. 2000; 7(3): 191); Guillain-Barre syndrome and auto-immune neuropathies (Kusunoki S. Am J Med Sei. 2000; 319(4): 234), myasthenia, Lambert-Eaton myasthenic syndrome (Takamori M. Am J Med Sei. 2000; 319(4): 204); paraneoplastic neurological diseases, cerebellar atrophy, paraneoplastic cerebellar atrophy and stiff-man syndrome (Hiemstra H S. et al., Proe Nat Acad Sci units S A 2001; 98(7): 3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. J. Rev Neural (Paris) 2000; 156(1): 23); dysimmune neuropathies (Nobile-Orazio E. et al., Eleetroencephalogr Clin Neurophysiol Suppl 1999; 50: 419); acquired neuromyotonia, arthrogryposis multiplex congenita (Vincent A. et al., Ann N Y Acad Sci. 1998; 841: 482), neuritis, optic neuritis (Soderstrom M. et al., J Neurol Neurosurg Psychiatry 1994; 57(5): 544) and neurodegenerative diseases.

Examples of auto-immune muscular diseases comprise myositis, auto-immune myositis and primary Sjogren's syndrome (Feist E. et al., Int Arch Allergy Immunol 2000; 123(1): 92) and smooth muscle autoimmune disease (Zauli D. et al., Biomed Pharmacother 1999; 53(5-6): 234).

Examples of auto-immune nephric diseases comprise nephritis and auto-immune interstitial nephritis (Kelly C J. J Am Soc Nephrol 1990; 1 (2):140).

Examples of autoimmune diseases related to reproduction comprise repeated fetal loss (Tincani A. et al., Lupus 1998; 7 Suppl 2: S107-9).

Examples of auto-immune connective tissue diseases comprise ear diseases, autoimmune ear diseases (Yoo T I et al., Cell Immunol 1994; 157(1): 249) and auto-immune diseases of the inner ear (Gloddek B. et al., Ann N Y Acad Sei 1997; 830: 266).

Examples of systemic autoimmune diseases comprise systemic lupus erythematosus (Erikson J. et al., Immunol Res 1998; 17(1-2): 49) and systemic sclerosis (Renaudineau Y. et al., Clin Diagn Lab Immunol. 1999; 6(2): 156); Chan O T. et al., Immunol Rev 1999 June; 169: 107).

Examples of transplantation-related diseases include, but are not limited to, graft rejection, chronic graft rejection, subacute graft rejection, hyperacute graft rejection, acute graft rejection and graft-versus-host disease (GVHD).

Examples of inflammatory/inflammation-associated diseases include, but are not limited to, restenosis following percutaneous transluminal coronary angioplasty (PTCA), restenosis following PTCA with stent implantation, myocardial infarction, inflammation associated with mechanical injury, neurodegenerative diseases, ulcers, prosthetic implants, menstruation, septic shock, anaphylactic shock, toxic shock syndrome, cachexia, gangrene, musculo-skeletal inflammation, idiopathic inflammation.

In addition, the preparation of the present invention can be used to treat inflammation in animals, such as arthritis in horses involved in equine competition or other inflammatory disease occurring in animals.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

FIGURES

FIG. 1. Dot plots of CD11b+F4/80+ macrophages stained with CD11b and F4/80-specific antibodies and analyzed by FACS either before plastic adherence step or after plastic adherence step (A). Thymic cells were submitted to apoptosis induction 6 hours before co-culture with enriched macrophages and demonstrated 57% of apoptosis (annexin V staining and 7-AAD exclusion) and few necrotic cells (7-AAD & annexin V positive cells) (B). Dot plots representative of 5 independent experiments showing similar results.

FIG. 2. SuperMApo (MApoSup) was quantified for the presence of active and total TGF-β and IL-10 (A), IL-1β and TNF (B) by ELISA, compared to the supernatants issued from the culture of macrophages (Macro) or apoptotic cells (Apo) alone respectively. Mean+/−sem of 3 to 11 independent experiments. Differences were assessed by paired t test and p<0.05 was considered as significant.

FIG. 3. Arthritic mice were treated by SuperMApo at day 30 and demonstrated a significant reduction in terms of pathological score (p<0.001; A). In another arthritis experiment, arthritic mice received either standard SuperMApo treatment (B, D) or SuperMApo in 2 times 1 ml or lyophilized (10 times 200 µl) (C, D). Such treatments demonstrated a significant resolution of the arthritic score (B, C; paired t test). Mean of 5 mice per group+/−sem. Results from independent experiments.

FIG. 4. The percentages (%) and numbers (×10e6) of Foxp3+ Treg, IFN+ Th1 and IL-17+ Th17 cells were assessed from lymphoid organs and in particular in the spleen (A, B) at time of sacrifice by FACS (A) and after a restimulation culture period in the presence of collagen (B). Differences have been assessed by student t test. Data issued from 1 representative experiment out of 2 showing similar results.

Figure 5:
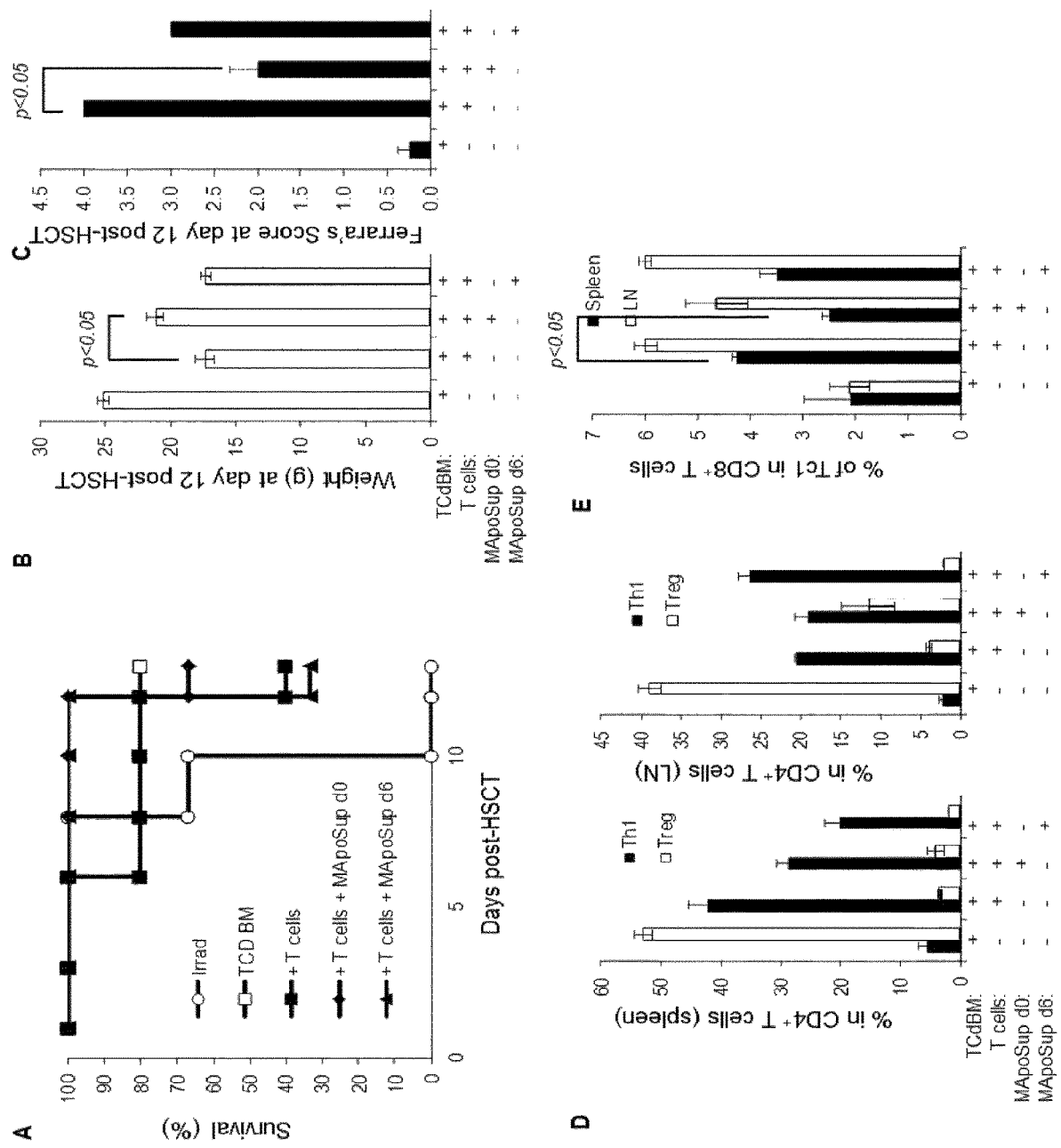

FIG. 5. Mice were submitted to HSCT and survival (A) weight loss (B), Ferrara's score (C) and Th1, Treg (D) and Tc1 cells (E) were assesses in the different groups: conditioned mice (Irrad), mice receiving T cell-depleted BM (TCD BM) alone or in addition to day 6 T cell injection (+T cells) with or without SuperMApo treatment either started at day 0 (MApoSup d0) or day 6 (MApoSup d6). Mean+/−sem of all mice per group. Five mice per group. Differences were assessed by student t test, p<0.05 was considered as significant.

Figure 6:
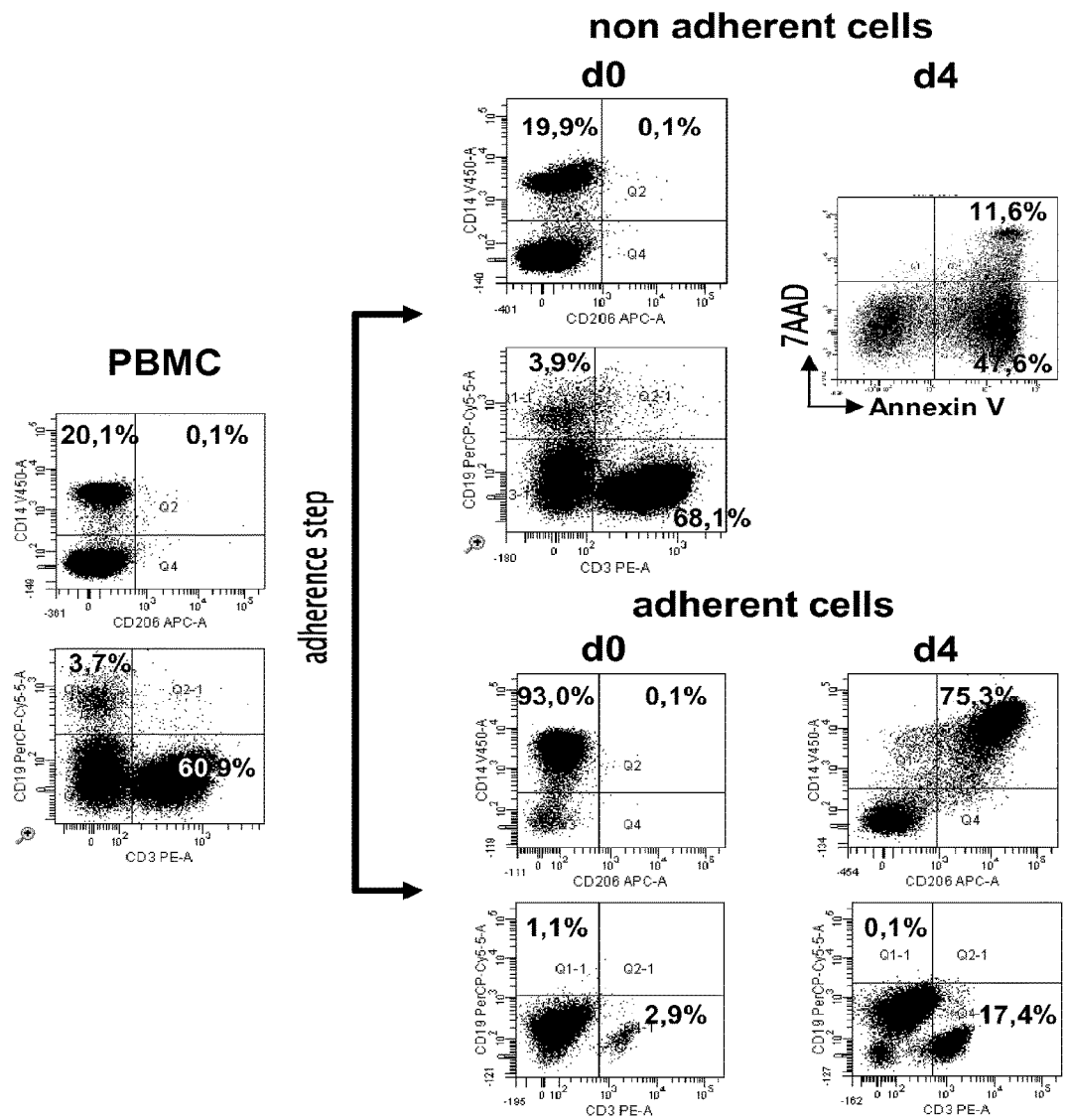

FIG. 6. After collection from buffy coat or cytapheresis, PBMC were submitted to plastic adherence and then cultured or not in the presence of M-CSF. Non adherent cells were irradiated at day 2 and apoptosis evaluated by FACS at day 4 using annexin V staining and 7-AAD exclusion. Percent of CD3+ T cells, CD19+ B cells, CD14+CD206− monocytes and CD14+CD206+ macrophages were assessed as indicated and percentages of each population were given in the quadrants.

Figure 7:
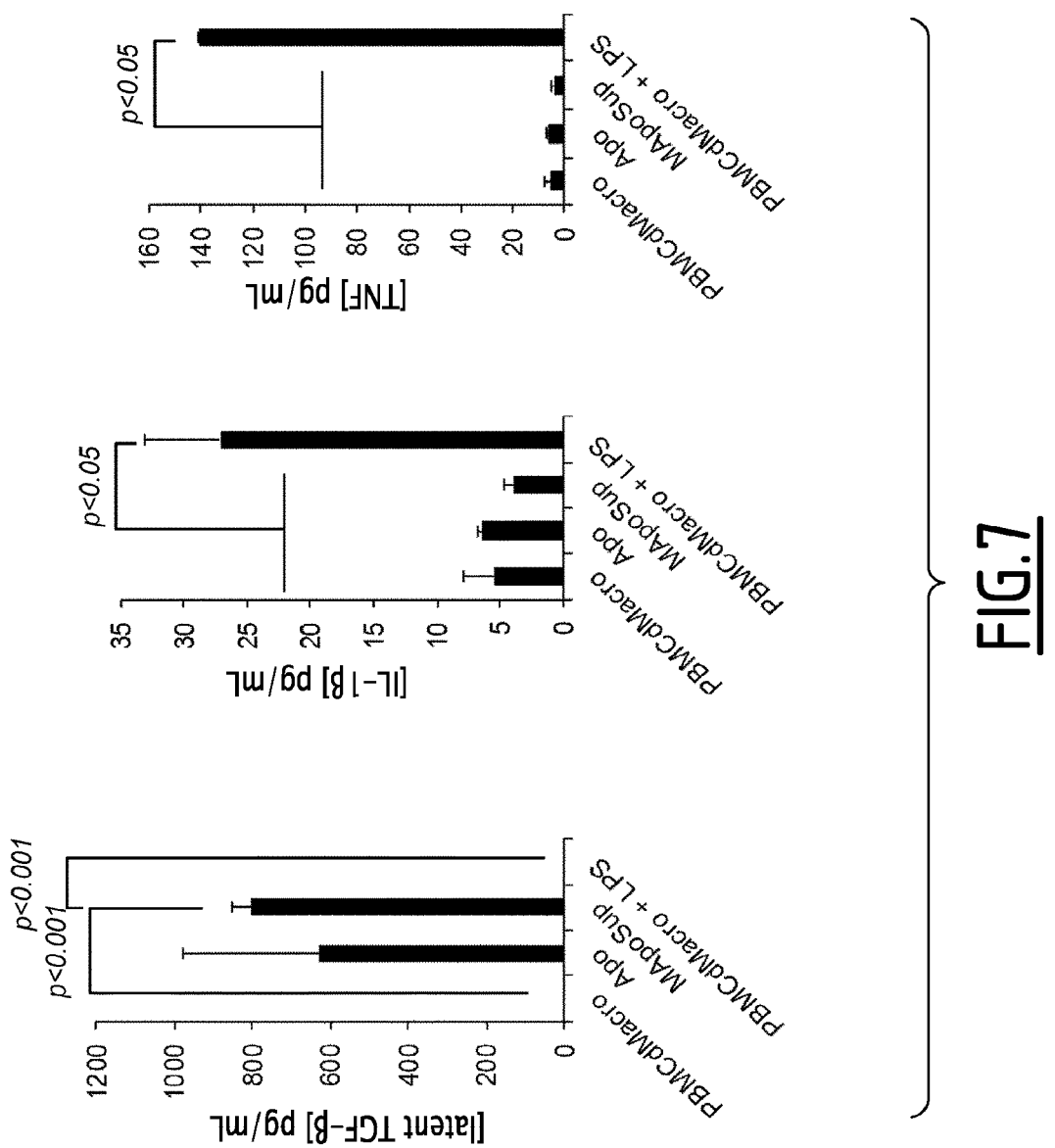

FIG. 7. Human SuperMApo (MApoSup) was quantified for the presence of latent TGF-β, IL-1β and TNF by ELISA and compared to supernatant issued from the culture of apoptotic cells alone (Apo) or macrophages alone (PBMCd-Macro) or macrophages stimulated with LPS (PBMCd-Macro+LPS). Differences were assessed using student t test and a p<0.05 was considered as significant. Mean+/−sem of 3 to 7 independent experiments.

Figure 8:
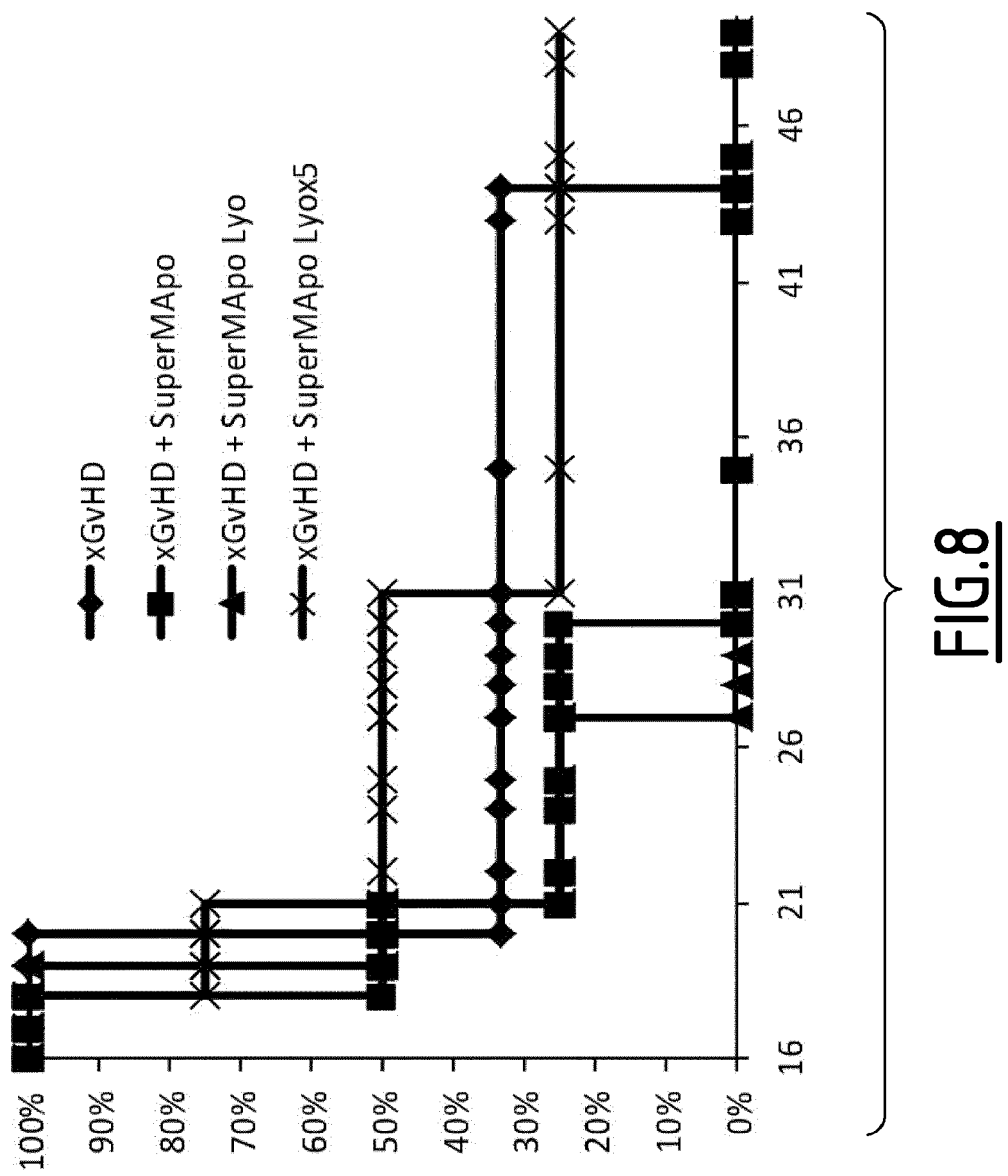

FIG. 8. Xenogeneic GvHD occurrence in NOG mice after injection of PBMC was evaluated using Ferrara's score and survival was assessed between groups: mice developing xGvHD not treated (xGvHD) or treated with either raw Super MApo (+SuperMApo) or with lyophilized and resuspended SuperMApo (+SuperMApo Lyo) or lyophilized and 5 times concentrated SuperMApo (+SuperMApo Lyox5). Three to 4 mice per group.

FIG. 9. Arthritic mice were treated by SuperMApo issued from DBA1 (red circles; CIA+SuperMApo) or C57Bl/6 mice, fresh (black circles; CIA+SuperMApo B6), lyophilized and reconstituted (black triangles; CIA+SuperMApo B6 Lyo) or lyophilized and concentrated 5 times (black diamonds, CIA+SuperMApo B6 Lyox5) at day 38 and demonstrated a significant and long term reduction in terms of pathological score compared to untreated arthritic mice (open circles, CIA) (***=p<0.001; CIA vs all groups, 1 way ANOVA followed by Tukey's multiple comparison test; A).

In another arthritis experiment, arthritic mice (CIA; open circles) received either standard SuperMApo treatment (black circles; CIA+SuperMApo) or apoptotic cell culture supernatant (black triangles; CIA+ApoSup) or macrophage culture supernatant (black diamonds; CIA+MacroSup) or the last two treatment together (open triangles; CIA+MacroSup+ApoSup) (B). Excepted SuperMApo treatment, other treatments did not favor significant resolution of the arthritic score (***=p<0.001; CIA vs CIA+SuperMApo, 1 way ANOVA followed by Tukey's multiple comparison test). Mean of 5 mice per group+/−sem. Results from 1 out of 2 independent experiments showing similar differences.

Figure 10:
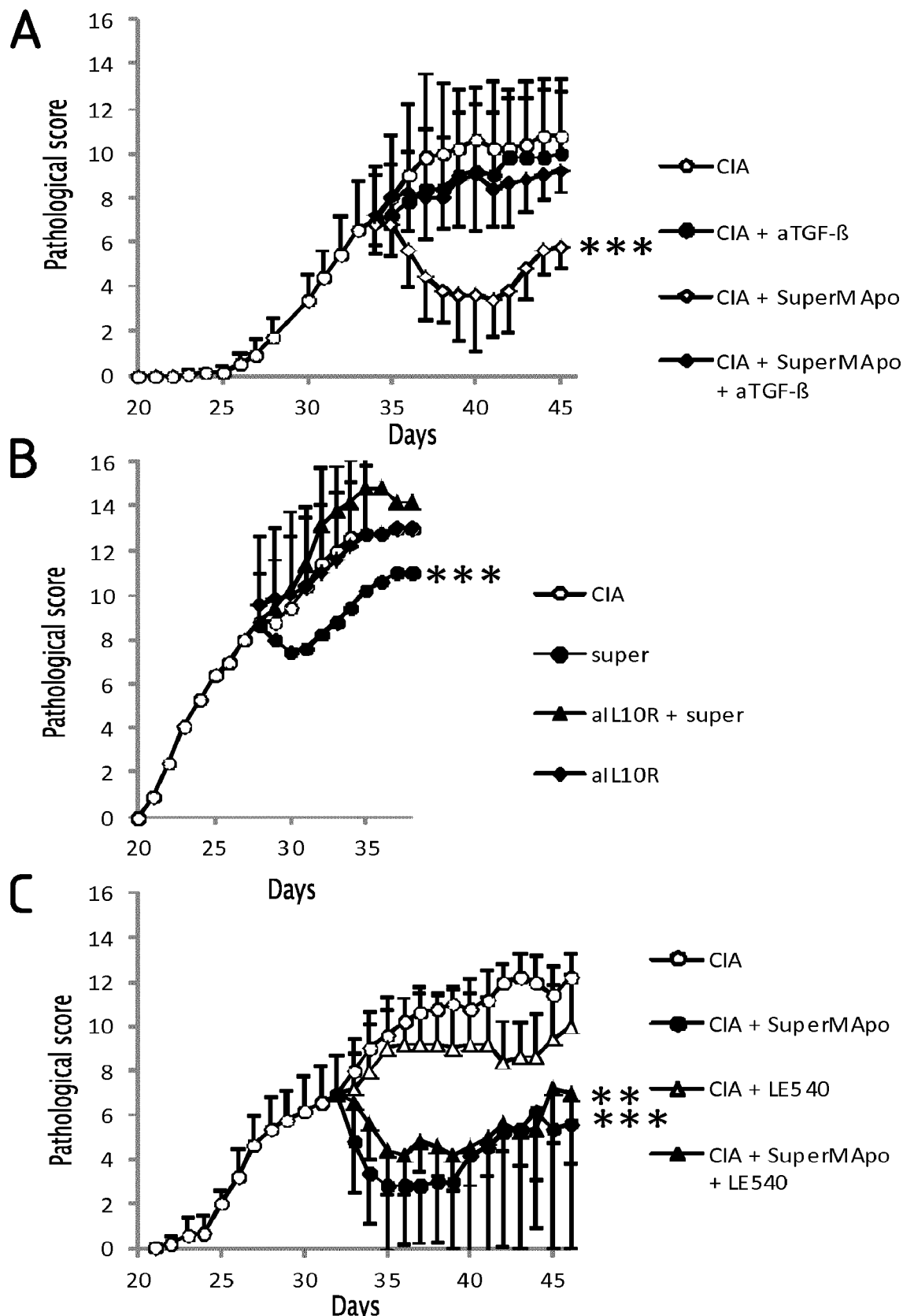

FIG. 10. A. Arthritic mice (CIA; open circles) were treated at day 34 by SuperMApo (CIA+SuperMApo; open diamonds) and received or not anti-TGF-β blocking antibody (αTGF-β). Anti-TGF-β antibody strongly inhibited the therapeutic effect of SuperMApo on the resolution of arthritis. *=p<0.001 CIA+SuperMApo vs all groups, 1 way ANOVA followed by Tukey's multiple comparison test. In another arthritis experiment (B), arthritic mice (CIA; open circles) were treated at day 28 by SuperMApo (super; black circles) and received or not anti-IL-10 receptor blocking antibody (aIL10R). Anti-IL-10R antibody strongly inhibited the therapeutic effect of SuperMApo on the resolution of arthritis. *=p<0.001 CIA+SuperMApo vs all groups, 1 way ANOVA followed by Tukey's multiple comparison test. In another arthritis experiment (C), arthritic mice (CIA; open circles) were treated at day 33 by SuperMApo (CIA+ SuperMApo; black circles) and received or not retinoic acid receptor antagonist LE540 (LE540). Retinoic acid antagonist did not inhibit the therapeutic effect of SuperMApo on the resolution of arthritis. *=p<0.001 CIA+SuperMApo vs all groups; =p<0.01 CIA+SuperMApo+LE540 vs CIA+LE540; 1 way ANOVA followed by Tukey's multiple comparison test. Mean of 5 mice per group+/−sem.

Figure 11:
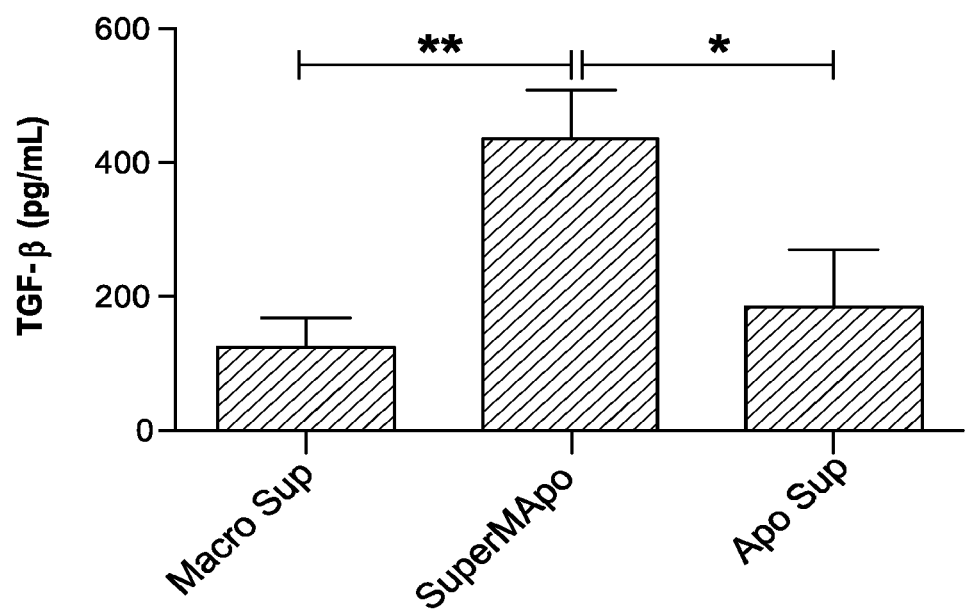

FIG. 11. TGF-β has been quantified in human SuperMapo by ELISA and compared to the levels of TGF-β in the supernatants of apoptotic cell (Apo Sup) or macrophage (Macro Sup) cultures. Mean+/−sem, n=8 independent experiments; *=p<0.05, **=p<0.01 (paired t test).

Figure 12:
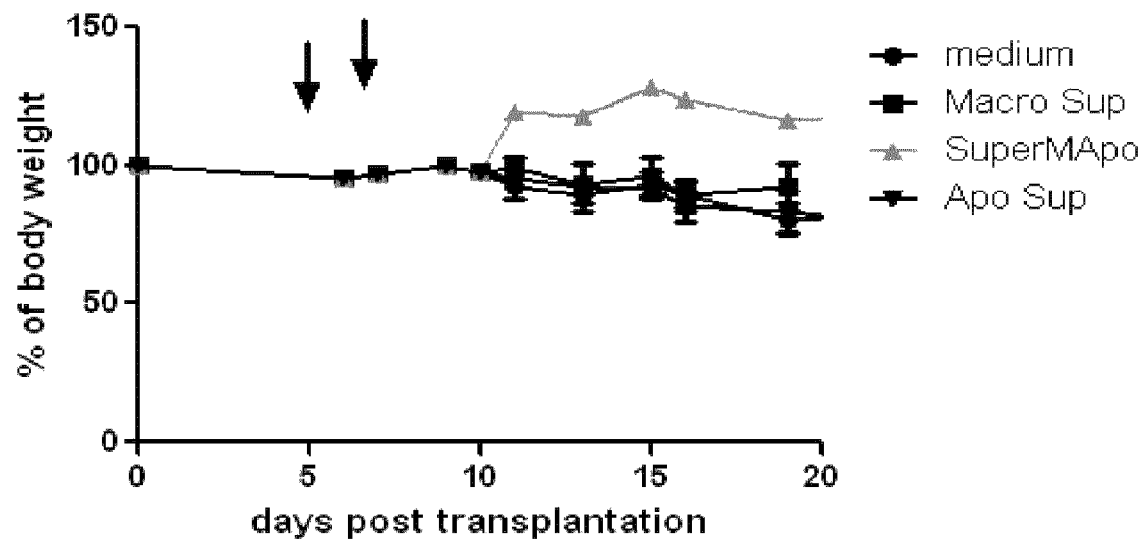

FIG. 12. Xenogeneic GvHD (xGvHD) occurrence in NOG mice after injection of PBMC was attested by weight loss between mice developing xGvHD untreated (medium; black circles) or receiving days 5 and 7 SuperMApo (SuperMApo; green triangles) or supernatants from either macrophage (Macro Sup; black squares) or apoptotic cell culture (Apo Sup; black triangles). Mean+/−sem, 4 to 5 mice per group. SuperMApo treatment allowed a protection against weigh loss in mice developing xGvHD.

Figure 13:
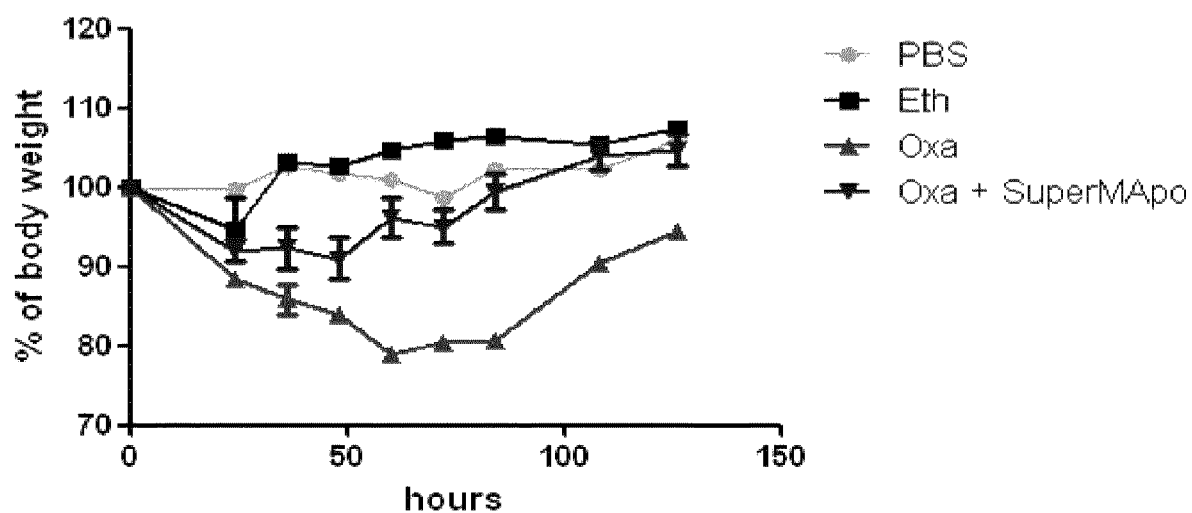

FIG. 13. Xenogenic acute intestinal inflammation occurrence in NOG mice after injection of PBMC and sensitization and injection of oxazolone was attested by weight loss between mice developing colitis untreated (Oxa; red triangles) or receiving SuperMApo (SuperMApo; blue triangles) at the time of oxazolone intra-rectal injection. Control groups are mice receiving oxazolone vehicule ethanol (Eth, black squares) or PBS (gray circles). Mean+/−sem, 4 to 5 mice per group. SuperMApo treatment allowed strong prevention of weight loss in mice developing colitis.

EXAMPLES

Reference is now made to the following examples, which together with the above descriptions illustrate the invention in a non-limiting fashion.

Example 1: Treatment of Arthritis Using SuperMApo Treatment

Materials and Methods
Induction and Scoring of Arthritis

DBA/1 susceptible mice were immunized by subcutaneous injection at the tail base with 100 μL of bovine type II collagen (200 μg/mL; MD Bioproducts, Zurich, Switzerland) emulsified in CFA (4 mg of *Mycobacterium* toxin resuspended in 1 mL of IFA, Sigma-Aldrich). Arthritis developed at day 25-28 after collagen immunization in all mice.

Arthritis severity was determined by daily visual examination of the paws as follows: each limb was scored on a scale of 0-4, where 0=normal paw, 1=swelling of one digit, 2=swelling of one or more digits erythema and severe swelling involving the entire paw. The clinical score for each mouse was the result of the sum of the 4 limbs (maximum score 16).

Four to five days after the appearance of the first symptoms, mice received a daily dose ip of 200 μL of SuperMApo (supernatant from macrophage-apoptotic cell co-culture) for 6 consecutive days. After that, injections were assessed every two days. In some experiments, SuperMApo was lyophilized and reconstituted 5-time concentrated with distilled water and therefore injected only two times: the first injection the day after the appearance of the first symptoms and the second one 48 h later.

Lymphoid organs were harvested at time of sacrifice for effector CD4$^+$ T cells analysis by FACS. T cells from lymphoid organs were also stimulated for 24 and 48 h in culture in the presence of collagen (2 μg/ml) and T cell polarization was assessed by FACS and supernatants were collected. Joint destruction was determined by immunohistochemistry of ankle joints; back limbs were harvested, decalcified using RDO solution (Eurobio, Les Ulis, France) and fixed with 10% neutral formalin, embedded in paraffin and cut in 5 μm sections for H&S staining.

In some experiments, TGF-β was neutralized in vivo using clone 1D11 anti-TFG-$β_{1,2,3}$ antibody injected intraperitoneally (150 μg at the time of SuperMApo injection followed by 100 μg 48 h later), IL-10 signaling was neutralized using clone 1B1.2 anti-IL-10R antibody intraperitoneally (150 μg at the time of SuperMApo injection followed by 100 μg 48 h later), retinoic acid signaling was neutralized using LE540 antagonist (6 times every 2 days starting the day of SuperMApo treatment, 30 μg each time, orally).

Production of SuperMApo

Thymic cells were used as apoptotic cells. After isolation, thymic cells were submitted to a 35 X-Gray irradiation and cultured in complete DMEM culture medium for 6 hours to allow apoptosis to occur. In parallel, macrophages were isolated from the peritoneum cavity, washed and cultured in complete RPMI (10% FBS, Peni-Strepto, EAA, Hepes, NaP and 2-MercaptoEthanol). Macrophages and apoptotic cells were then washed and co-cultured for another 48 hour period in phenol-free X-vivo medium at a 1/5 macrophage/apoptotic cell ratio. Then, supernatant was collected, centrifuged to eliminate debris and freeze or lyophilized for conservation. Macrophages enrichment was confirmed using positive staining for F4/80 by FACS. Apoptosis was confirmed by FACS using positive staining for Annexin-V and 7AAD exclusion.

Cytokine Quantification

Cytokines were quantified in culture supernatants by ELISA using commercial kits following manufacturer's instructions: IL-1β (eBiosciences), IL-6 (R&D Systems), TGF-β1 (Promega, Madison, WI) and TNF (Biolegend).

Results

Macrophages issued from the peritoneal cavity of mice were enriched by plastic adherence (from 32 to >67% of F4/80+ macrophages, FIG. 1A) and the culture with apoptotic thymocytes. Apoptotic thymocytes were obtain from thymic cells submitted to 40 gray X-ray radiation and incubated in completed medium for 6 hours in order to allow apoptosis to occur (FIG. 1B). As showed FIG. 1B, apoptotic thymocytes demonstrated apoptosis (57%) as controlled by annexin V expression and 7-AAD exclusion. In parallel, engulfment of apoptotic cells by macrophages was assessed by fluorescent microscopy using CFSE-labeled apoptotic cells and PE-coupled F4/80-labeled macrophages. At t0, macrophages were observed close to apoptotic cells due to 1/5 ratio. Then after 24 hours of culture, mostly all apoptotic cells have been eliminated. This is attested by the presence of apoptotic cell-macrophage interactions as soon as after 6 hours of co-culture, followed by apoptotic cell engulfment by macrophages (6-12 hours) and the presence of apoptotic cell-derived debris within the macrophages after 24 hours.

After 48 hours, the supernatant of macrophage/apoptotic cell culture was collected (=SuperMApo) and quantified for the presence of cytokines. As shown in FIG. 2A, the supernatant was significantly enriched in TGF-β levels, both in active and latent forms of TGF-β, compared to the supernatants obtained from either macrophages or apoptotic cells cultured separately. In addition, IL-10 level was also increased compared to macrophages cultured alone and dramatically increased compared to apoptotic cells cultured alone (FIG. 2A). In sharped contrast, inflammatory cytokines were not detectable as IL-6 or at very low levels as IL-1β and TNF (FIG. 2B).

To determine composition in terms of cytokines, notably, a cytokine array was performed for the presence of 40 factors presented in SuperMApo. This was compared to the supernatants issued either from macrophages cultured alone or from apoptotic cells cultured alone, in the same time and medium conditions. Thus, SuperMapo revealed that the presence of increased levels of IL-1ra, TIMP-1, CXCL1/KC and CCL2/JE/MCP1 might be implicated in the tolerogenic role of SuperMApo to control inflammation, in addition to TGF-β and IL-10. It was then determined whether SuperMApo administration would be efficient to treat mice submitted to collagen-induced arthritis (CIA). Thus arthritis was induced in BDA1 susceptible mice by the injection of bovine type II collagen. After 25-26 days, arthritis occurred, attested by digit and paw swelling. Then at day 30, to be sure that arthritis was developing, SuperMApo treatment was initiated. Thus, when mice demonstrated an arthritic score of 5, they received 200 μL ip of SuperMApo daily for 6 days and then every two days for a total volume of 2 mL of SuperMApo per mice. This volume corresponds to supernatant issued from the culture of 1.10e6 macrophages with 5.10e6 apoptotic cells. Control CIA mice were in injected with PBS. All CIA mice were followed daily and scored for arthritis on a scale from 0 to 4 for each paw, as described (Bonnefoy F et al., J Immunol. 2011; 186(11): 6157).

Surprisingly, it was observed that SuperMApo treatment was very efficient to control CIA severity in mice and significantly reduced arthritic score (p<0.001, paired t test) (FIG. 3A). Of importance, even after the end of the treatment (day 44), arthritis did not increase and stayed controlled (FIG. 3A). The same experiment was repeated using a new production of SuperMApo in order to compare the posology of SuperMApo administration. Again, effect of SuperMApo on arthritis development was striking, showing a strong reduction of the pathology, to almost absence of score in some mice (FIG. 3B). In the same experiment two injections were compared (2 times 1 mL) to 10 times 200 μL (FIG. 3B, C). In addition, it was evaluate whether lyophilization of SuperMApo can affect its therapeutic effect. Thus, another group of CIA mice received the same treatment than in FIG. 3B but issued form SuperMApo that has been lyophilized, frozen and reconstituted for 10 injections. These data demonstrated first that SuperMApo treatment given in two doses is effective to prevent the disease (FIG. 3C, D), however not as good as ten injections (p=−0.008). Similarly, "lyophilized" SuperMApo treatment demonstrated a significant efficacy to diminish CIA score, compared to untreated mice (FIG. 3C, D). Nevertheless, lyophilized treatment demonstrated reduced capacity compared to fresh SuperMApo treatment. The inventors also evaluated long term protection and the therapeutic efficacy of SuperMApo issued from C57Bl/6 mice to treat DBA1 mice developing CIA. As shown in FIG. 9A, mice receiving "DBA1" lyophilized SuperMApo demonstrated a long term control of arthritis more than 60 days after treatment made of only two injections of lyophilized SuperMApo. In addition, "C57Bl/6" SuperMApo fresh, lyophilized, or concentrated was as efficient as "DBA1" SuperMApo to favor a long term control of arthritis. In order to determine factors responsible for the therapeutic effect of SuperMApo, we compared SuperMApo treatment to the supernatant issued from apoptotic cell culture, macrophage culture and to the addition of the two later. Arthritic mice receiving addition of apoptotic cell and macrophages supernatants did not demonstrate any decrease of their arthritic score compared to mice receiving SuperMApo suggesting that factors demonstrating a therapeutic activity were issued from macrophages eliminating apoptotic cells and not from each cell type cultured alone (FIG. 9B).

It was then determined whether immune cells implicated in the physiopathology of arthritis such as T cells were affected by the treatment. Leukocytes from lymphoid organs, spleen, draining lymph nodes (LN) and non-draining LN were harvested and tested ex vivo for the presence of Th1, Th17 or Treg cells as well as after 48 additional hours of culture in the presence of collagen. Ex vivo, the percentage of Treg within the CD4$^+$ T cells in the spleen is significantly increased (p=0.007; student t test) and this increase is also observable in total number of Treg in the spleen. In parallel, Th1 and Th17 cells demonstrated a slight decrease in both percentages and numbers (FIG. 4A). Those differences are not evident in the draining and non-draining lymph nodes (data not shown). To observe the pathogenic T cells, the cells were cultured in presence of collagen for 48 hours and tested them for Foxp3, IFN and IL-17 expression by FACS. As shown in FIG. 4B, Treg (Foxp3$^+$ CD4$^+$ T cells) are significantly increased in the spleen and Th1 and Th17 pathogenic cells demonstrated percentage reduction in the spleen also.

Since Treg are increased after SuperMApo treatment, the role of TGF-β, IL-10 and retinoic acid (RA) in such process were evaluated. Therefore, TGF-β$_{1,2,3}$ was neutralized using blocking antibody, IL-10 using IL-10R blocking antibody and retinoic acid using LE540 RA receptor antagonist. As shown in FIG. 10A, B, neutralization of TGF-β and IL-10 signaling strongly inhibited the effect of SuperMApo treatment on CIA. However, inhibition of retinoic acid (RA) signaling did not affect the therapeutic effect of SuperMApo (FIG. 10C). The data suggested that SuperMApo therapeutic efficacy relied on direct or indirect induction of TGF-β and IL-10 dependent mechanisms.

Conclusion

These data demonstrated that the SuperMApo, culture supernatant issued from the culture of macrophages with apoptotic cells, when injected in mice decreases inflammation. Arthritic mice receiving such a treatment demonstrated a strong reduction of pathology in terms of clinical score and histological lesions. This significant decrease is associated with an increase of regulatory T cells notably in the spleen. Such a treatment might depend on the presence of IL-1ra, TIMP-1, CXCL1/KC and CCL2/JE/MCP1, as shown by proteome analysis, as well as on TGF-β and IL-10, as shown by ELISA. Altogether, the data show that treatment of inflammatory disease such as arthritis using SuperMApo is an efficient treatment to control pathology. Of importance, complete remission seems to be reachable after optimizing SuperMApo treatment.

Example 2: SuperMApo Treatment the Day of Transplantation Delayed GvHD Occurrence and Reduced GvHD Severity Graft versus Host disease (GvHD) is a toxic and mostly dead-end adverse of hematopoietic stem cell transplantation (HSCT) in the treatment of hematological malignancies. Such event arises when donor T cells, help by recipient antigen presenting cells, recognize and destruct recipient tissues. Acute GvHD is considered as an inflammatory process that can lead to a chronic form of GvHD more associated with autoimmune features. In this context, it was tested whether SuperMApo treatment would be able to counteract inflammation and prevent or delay GvHD.

Material and Methods

Mice and GvHD Experimental Model

After a myeloablative conditioning regimen (7 Gy, X-ray irradiation) at day −1, Balb/c mice received C57Bl/6 bone marrow cells (10.10e6 cells/mouse) depleted with T cells using MACS technology. Six days later, recipient mice were injected with C57Bl/6 T cells (1.10e6 cells/mouse) to favor GvHD occurrence. Mice were housed in sterile micro isolator cages within pathogen-free animal facility, receiving sterile food and water ad libitum, water was supplemented with neomycin (1.1 g/l), 1 day before irradiation. Recipient mice were then followed daily for survival and GvHD sign occurrence according to Ferrara's score (Cooke K R et al. Blood. 1996; 88(8): 3230). The score of Ferrara includes evaluation of weight, activity, posture, skin and fur integrity of the mice. Recipient mice received SuperMApo treatment the day of transplantation (d0) or the day of T cell injection (d6), comprising every 2 days ip injections of 200 μL of SuperMApo for a total of 10 injections. SuperMApo was produced as described in Example 1. Some mice were sacrificed at day 13 to evaluate immune populations in the spleen and lymph nodes.

Results and Conclusion

The data demonstrated that mice receiving T cells developed GvHD compared to mice receiving T cell-depleted BM (TCdBM) as attested by a decrease survival rate (FIG. 5A), a loss of weight (FIG. 5B) and a higher Ferrara's score (FIG. 5C) at day 12 post-HSCT. In contrast to mice developing GvHD, mice treated with SuperMApo at d0 demonstrated a better survival curve (FIG. 5A) comparable to mice receiving only TCdBM, a less profound weigh loss (p<0.05; FIG. 5B) and a decreased GvHD score (p<0.05; FIG. 5C). Thus, SuperMApo treatment the day of transplantation favors an immunomodulatory environment, as well as less sensitivity to day 6 T cell-induced GvHD. This is in contrast with SuperMApo treatment at day 6 in which the survival was not ameliorated (FIG. 5A). Indeed, mice demonstrated similar weight loss and score compared to mice developing GvHD (FIG. 5B, C). These data suggested that SuperMApo treatment better control GvHD occurrence when injected before T cell injection, whereas SuperMApo treatment at the time of T cell injection seems not efficient to prevent GvHD occurrence. The better survival and amelioration of GvHD score in mice treated by SuperMApo at day 0 is associated with both less Th1 cells in the spleen and a Treg increase within the lymph nodes (FIG. 5D) as compared to mice receiving TCdBM+T cells. In addition, less IFN$^+$CD8$^+$ Tc1 cells were observable in the spleen and lymph nodes of such mice compared to mice developing GvHD (FIG. 5E). The data strongly demonstrate the efficacy of SuperMApo treatment to moderate GvHD.

Example 3: Human SuperMApo Treatment Delays Xenogeneic GvHD

In order to demonstrate that SuperMApo produced from human cells (hSuperMApo) exhibits the same efficacy to treat inflammation than mouse SuperMApo, it was evaluated whether hSuperMApo treatment is effective to counteract Graft versus Host disease (GvHD) occurrence in a xenogeneic experimental model of GvHD. First, hSuperMApo was qualified in terms of cytokine content and then tested for its efficacy in vivo. Then, it was evaluated whether hSuper- MApo treatment was able to inhibit human leukocyte induced GvHD in immunodeficient mice.

Materials and Methods

Production of hSuperMApo

Human SuperMApo was issued from the co-culture of macrophages derived from peripheral blood mononuclear cells (PBMC) cultured with apoptotic PBMC. Thus, PBMC were isolated from cytapheresis bag from healthy volunteer through Ficoll gradient centrifugation. Then PBMC were plated for 90 min in complete RPMI culture medium (10% FBS, 1% Penicillin/Streptomycin). Then, non-adherent cells were removed and rendered apoptotic using a 35 Gy dose of X-ray irradiation and cultured in complete RPMI milieu for 4 days (including cell wash after the first 48 hrs of culture), in order to allow apoptosis to occur. In parallel, adherent cells were cultured in complete RPMI milieu supplemented with 50 μg/mL of recombinant human M-CSF for 4 days including cell wash after the first 48 hrs. At the end of the 4-day culture period, monocyte-derived macrophages and apoptotic cells were washed and cultured together in X-vivo medium for again 48 hours at a one macrophage to 5 apoptotic cell ratio. Then supernatant from the latter culture was collected, centrifuged to eliminate cells and debris and frozen or lyophilized for conservation and subsequent use.

Xenogeneic GvHD

Six to 8 week-old NOG mice (NOD.Cg-Prkdc$^{scid}$ Il2rg$^{tm1Sug}$/JicTac; Taconic) were submitted to a 2 Gy X-ray irradiation 24 hours before receiving iv injection of $10.10^{e}6$ PBMC isolated from healthy donors. Mice were housed in sterile micro isolator cages within pathogen-free animal facility, receiving sterile food and water ad libitum, water was supplemented with neomycin (1.1 g/l), 1 day before irradiation. GvHD occurrence was evaluated daily according to Ferrara's score (Cooke K R et al. Blood. 1996; 88(8): 3230). When mice presented moderate GvHD score, treatment with hSuperMApo was initiated, consisting in a daily injection of 200 μL of hSuperMApo for 5 days followed by an injection every 2 days for the next 10 days, for a total of 10 injections.

Cytokine Quantification

Cytokines were quantified in hSuperMApo, serums or culture supernatants by ELISA using commercial kits following manufacturer's instructions: IL-1β (eBiosciences), TGF-β1 (Promega, Madison, WI) and TNF (eBiosciences).

Results and Conclusion

This process allowed the inventors to obtain hSuperMApo in 6 days from peripheral blood mononuclear cells (PBMC). Four days are necessary to obtain PBMC-derived macrophages using M-CSF addition in the culture and 2 more days are necessary for the co-culture of PBMC-derived macrophages with apoptotic cells, corresponding to the non-adherent PBMC isolated at day 0. Our process demonstrated efficiency to produce a standardized hSuperMApo independently of the donor or the source of PBMC (cytapheresis or buffy coat; data not shown). First the plastic-adherence step was demonstrated sufficient to obtain a significant starting population of enriched monocytes (20 to 93% of CD14+ cells after adherence on plastic culture dish; Table 1 & FIG. 6). In addition, such adherent cells demonstrated a very low presence of B and T cells (1.0% of CD19+ B cells and 12.8% of CD3+ T cells; Table 1 & FIG. 6). After 4 days of culture of adherent cells in the presence of M-CSF, the proportion of monocytes derived-macrophages was significantly increased from 0.1% to 77.7% of CD14+CD206+HLA-DR+ macrophages (Table 1). At that time, monocyte-derived macrophages were co-cultured with apoptotic non-adherent PBMC (47.6% apoptotic as shown by annexin V staining and 7AAD exclusion; FIG. 6) to produce SuperMApo during 48 hours. The collected supernatant, ie SuperMApo, was then quantified for anti-inflammatory and inflammatory cytokines. As shown in FIG. 7, SuperMApo contained a certain amount of latent TGF, significantly more than in the culture supernatant of monocyte-derived macrophages alone or monocyte-derived macrophages treated in inflammatory conditions (+LPS). This was confirmed and found significant compared to apoptotic cell or macrophage culture supernatants in a new set of production of hSuperMApo (n=8 independent productions; FIG. 11). On the opposite, SuperMApo contained trace or low level of inflammatory cytokines such as IL-1β or TNF (FIG. 7). Compared to the supernatant issued from monocyte-derived macrophages stimulated with LPS, SuperMApo contained significantly lower amount, closed to the limit of detection, of such inflammatory cytokines (FIG. 7). To evaluate the efficacy of SuperMApo to decrease inflammation in human setting, NOG mice received human PBMC in order to induce xeno GvHD (xGvHD). At day 16 post injection, 9 out of 24 mice were died from GvHD. The 15 other xGvHD mice were then split in 4 groups and treatments with SuperMApo were started on day 17. Treatment groups included PBS-treated xGvHD group (n=3), SuperMApo-treated (n=4), lyophilized SuperMApo-treated (n=4) and lyophilized+5 time concentrated SuperMApo-treated xGvHD group (n=4). During the days following treatments, some mice still died from xGvHD in the different groups (FIG. 8). However, 50% of the mice survived in the group of xGvHD mice receiving SuperMApo lyophilized 5 times compared to other groups, during more than 15 days following xGvHD occurrence (FIG. 8). This result suggested that the factors allowing inflammation reduction/prevention, in the SuperMApo, were maybe not enough concentrated in the raw SuperMApo and sufficient in the SuperMApo lyophilized 5 times, allowing efficacy in the prevention of xGvHD. At time of sacrifice, 1 mice survived in the group receiving SuperMApo lyophilized 5 times (FIG. 8). Indeed in an additional experiment, mice receiving concentrated SuperMApo demonstrated a regain of weight attesting of better survival (FIG. 12). Mice developing GvHD and receiving macrophage culture supernatant or apoptotic cell culture supernatant were not protected and demonstrated a continuous weight loss the days following corresponding treatment injection (FIG. 12). Altogether, the data suggested that the SuperMApo treatment will prove efficient to diminish inflammation in human, in particular to prevent GvHD occurrence and increase survival after HSCT.

TABLE 1

|  | PBMC | Adherent cells, d0 | Non-adherent cells, d0 | Adherent cells, d4 |
| --- | --- | --- | --- | --- |
| CD3$^+$ T cells | 51.1% ± 6.0 | 12.8% ± 8.9 | 63.3% ± 6.3 | 15.0% ± 2.4 |
| CD19$^+$ B cells | 4.1% ± 1.0 | 1.0% ± 0.6 | 4.0% ± 1.2 | 0.1% ± 0.1 |
| CD14$^+$HLA-DR$^+$CD206$^-$ monocytes | 23.7% ± 2.6 | 75.2% ± 16.1 | 20.3% ± 4.0 | 4.4% ± 0.2 |

TABLE 1-continued

| | PBMC | Adherent cells, d0 | Non-adherent cells, d0 | Adherent cells, d4 |
|---|---|---|---|---|
| CD206+CD14+HLA-DR+ macrophages | 0.2% ± 0.1 | 0.3% ± 0.3 | 0.1% ± 0.0 | 77.7% ± 2.4 |

T, B, monocytes and macrophages were evaluated at the different step of SuperMApo production by FACS and the data were given as percentage within the total population. Mean+/−sem from 2 to 4 different experiments.

Example 4: Human SuperMApo Treatment Alleviated Acute Intestinal Inflammation

In order to evaluate whether human SuperMApo was able to control inflammation in another "humanized" mouse model, SuperMApo treatment was evaluated in oxazolone and ethanol-induced colitis in NOG mice engrafted with human peripheral blood mononuclear cells.

Materials and Methods

Human SuperMApo was produced as described in Example 3. Presence of TGF-β was controlled in Super-MApo before use.

Experimental Model of Colitis:

Peripheral blood was collected from healthy patient, using Ficoll density centrifugation. Human PBMC were isolated, washed and resuspended in phosphate-buffered saline (PBS) at a concentration of 20.10e6/ml. NOG mice, 6-16 weeks old, were engrafted with 200 ml of the cell suspension by intravenous injection. The animals rested for 7 days prior to first sensitization with oxazolone.

Then NOG mice (5 mice per group) 7 days post-engraftment, were anaesthetized with isoflurane, a 2×2-cm skin area (region lumbalis) was shaved and depilated on day 1. Animals were presensitized by topical application of 20 ml 5% oxazolone (4-ethoxymethylene-2-phenyl-oxazolin-5-one) (Sigma-Aldrich, Deisenhofen, Germany) in 100% ethanol. On day 8 mice were challenged with 150 ml 1% oxazolone in 50% ethanol/H2O by rectal application with a balloon catheter under anaesthesia with isoflurane. The control group was treated with ethanol for presensitization or 50% ethanol/H2O for rectal application. An additional control group was treated with PBS. Mice were inspected twice daily and killed on day 16.

Results and Conclusion

One hour after intra-rectal administration of oxazolone, mice received the first injection of SupertMApo (PBS in the control group) and then every 24 h for a total of 4 injections (300 µl of SuperMApo or PBS each injection). Mice receiving SuperMApo demonstrated a protection against weight loss compared to mice receiving PBS (FIG. 13). These data demonstrated that SuperMApo allowed the control of inflammation in a model of acute intestinal colitis. This opens application area of SuperMApo such as in inflammatory intestinal diseases to control inflammation.

The invention claimed is:

1. A composition comprising a supernatant, the supernatant obtained by:
   a) providing macrophages;
   b) providing apoptotic cells;
   c) optionally washing the cells from step a) and b);
   d) co-culturing the cells of step a) and b) for hours or days; and
   e) separating the supernatant from the cells.

2. A composition comprising a supernatant, the supernatant obtained by:
   a) providing dendritic cells;
   b) providing apoptotic cells;
   c) optionally washing the cells from step a) and b);
   d) co-culturing the cells of step a) and b) for hours or days; and
   e) separating the supernatant from the cells.

3. A composition comprising a supernatant, the supernatant obtained by:
   a) providing an amount of viable phagocytes, the viable phagocytes being phagocytes that have not been subjected to an apoptosis induction;
   b) providing apoptotic cells;
   c) optionally washing the cells from step a) and b);
   d) co-culturing the cells of step a) and b) until anti-inflammatory compounds are present; and
   e) separating the supernatant, which includes the anti-inflammatory compounds, from the cells.

4. The composition to claim 3, wherein the apoptotic cells from which the supernatant is obtained have been obtained by an apoptosis induction selected from the group consisting of hypoxia, ozone, heat, radiation, chemicals, osmotic pressure, pH shift, X-ray irradiation, gamma-ray irradiation, UV irradiation, serum deprivation, corticoids and combinations thereof.

5. The composition to claim 3, wherein the apoptotic cells from which the supernatant is obtained have been obtained by an apoptosis induction selected from the group consisting of X-ray irradiation, gamma-ray irradiation, UV irradiation, and combinations thereof.

6. The composition according claim 3, wherein the apoptotic cells from which the supernatant is obtained are leukocytes.

7. The composition according claim 3, wherein the phagocytes from which the supernatant is obtained are derived from peripheral blood mononuclear cells (PBMC).

8. The composition according claim 3, wherein the phagocytes from which the supernatant is obtained are macrophages.

9. The composition according claim 3, wherein the phagocytes from which the supernatant is obtained are dendritic cells.

10. The composition to claim 6, wherein the phagocytes are from a phagocyte cell preparation in which the phagocytes represent 20% to 100% of the cells of the phagocyte cell preparation.

11. The composition to claim 10, wherein the phagocytes and the apoptotic cells in the co-culture are present in a ratio ranging from 10:1 to 1:10.

* * * * *